(12) United States Patent
Deppermann et al.

(10) Patent No.: US 8,685,321 B2
(45) Date of Patent: Apr. 1, 2014

(54) AUTOMATED MULTI-STATION SMALL OBJECT ANALYSIS

(75) Inventors: Kevin L. Deppermann, St. Louis, MO (US); Ping Feng, St. Louis, MO (US); Matthew J. Weis, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 388 days.

(21) Appl. No.: 13/057,649

(22) PCT Filed: Aug. 5, 2009

(86) PCT No.: PCT/US2009/052780
§ 371 (c)(1),
(2), (4) Date: Apr. 20, 2011

(87) PCT Pub. No.: WO2010/017258
PCT Pub. Date: Feb. 11, 2010

(65) Prior Publication Data
US 2011/0195866 A1    Aug. 11, 2011

Related U.S. Application Data

(60) Provisional application No. 61/086,343, filed on Aug. 5, 2008.

(51) Int. Cl.
*G01N 35/02* (2006.01)
*A01C 1/00* (2006.01)
*G01N 35/04* (2006.01)

(52) U.S. Cl.
USPC ...... 422/65; 422/63; 422/67; 47/14; 209/592; 436/43

(58) Field of Classification Search
None
See application file for complete search history.

(56) References Cited

U.S. PATENT DOCUMENTS

| 5,424,036 A * | 6/1995 | Ushikubo ............... 422/64 |
| 2005/0058574 A1* | 3/2005 | Bysouth et al. ............. 422/63 |
| 2008/0038827 A1 | 2/2008 | Miller |

FOREIGN PATENT DOCUMENTS

| WO | 2006026467 | 3/2006 |
| WO | 2007039524 | 4/2007 |
| WO | 2007087183 | 8/2007 |

* cited by examiner

*Primary Examiner* — P. Kathryn Wright
(74) *Attorney, Agent, or Firm* — Polster, Lieder, Woodruff & Lucchesi, LC

(57) ABSTRACT

The present disclosure provides systems and methods for analyzing a plurality of samples of small objects. In various other embodiments, the system includes a staging console for supporting a plurality of sample trays. The system additionally includes a plurality of workstations that each includes a robotic container transfer subsystem for sequentially removing and replacing each of a plurality of sample containers arrayed in the sample trays, each sample container containing a sample of small objects. Each workstation additionally includes an automated analysis subsystem for sequentially receiving each container from the transfer subsystem, removing each sample from the respective container, acquiring data of each sample and returning each sample to the respective container. The system further includes a tray shuttle robot that distributes and retrieves the sample trays to and from the workstations.

40 Claims, 20 Drawing Sheets

AUTOMATED MULTI-STATION SMALL OBJECT ANALYSIS

RELATED APPLICATIONS

This application is a National Stage of International Application No. PCT/US2009/052780, filed Aug. 5, 2009, which claims priority to U.S. Provisional App. No. 61/086,343, filed on Aug. 5, 2008. The disclosures of which are incorporated herein by reference in their entirety

TECHNICAL FIELD

The present teachings generally relate to automated systems and methods for analyzing pluralities of small objects at a high rate of efficiency and speed.

BACKGROUND ART

The statements in this section merely provide background information related to the present disclosure and may not constitute prior art.

In the agricultural industry, and more specifically in the seed breeding industry, it is important for scientists to be able to analyze seeds with a high throughput rate. By this it is meant that the analysis of the seeds preferably occurs not only quickly, but also with a high total volume. For example, in seed breeding, large numbers of seeds are analyzed to determine whether the seeds possess particular traits. Typically, seeds are manually processed to obtain a seed sample, then visually examined and/or analyzed using selected manually operated analysis instruments. Such manual seed analysis procedures are tedious, cumbersome, lengthy, labor intensive and subject to human error.

SUMMARY OF THE INVENTION

The present disclosure provides systems and methods for analyzing a plurality of sets of small objects, for example seeds, to determine whether each set of objects possesses one or more desired traits. The methods are particularly adapted for automation, which provides greater efficiency and throughput than was previously practical.

In various other embodiments, the system includes a staging console structured to support a plurality of sample trays populated with a plurality of arrayed sample containers. Each sample container contains a respective object sample comprising a plurality of small objects. The system additionally includes a plurality of workstations that are structured and operable to analyze each object sample provided by each sample tray. Each workstation comprises a robotic container transfer subsystem that is structured and operable to sequentially remove and replace each of the sample containers arrayed in at least one of the sample trays. Each workstation additionally includes an automated analysis subsystem that is structured and operable to sequentially receive each sample container from the container transfer subsystem, remove each object sample from the respective sample container, analyze each respective object sample and return each object sample to the respective sample container. The system further includes a tray shuttle robot that is structured and operable to remove each sample tray from the staging console, distribute each sample tray to a corresponding one of the workstations, retrieve the sample trays from the workstations, and return each sample tray to the staging console.

In various other embodiments, the method includes supporting a plurality of sample trays populated with a plurality of arrayed sample containers on a staging console located at a tray staging location adjacent a home end of a guide track for a tray shuttle robot. Each sample container contains a respective object sample including a plurality of small objects. The method additionally includes distributing each sample tray to a corresponding one of a plurality of workstations located adjacent at least one side of the guide track, via automated operation of the tray shuttle robot along the guide track. The method further includes sequentially removing each sample container from the respective sample tray, removing each object sample from the respective sample container, and analyzing each object sample, via automated operation of the workstations. Furthermore, each object sample is returned to the respective sample container and each sample container is returned to the respective sample tray, via automated operation of the workstations. The method still further includes retrieving the sample trays from each workstation and returning each sample tray to the tray staging location, via automated operation of the tray shuttle robot along the guide track.

In yet other embodiments, the system can include a plurality of workstations structured and operable to analyze each of a plurality of object samples, each object sample comprising a plurality of small objects. Each workstation can include a robotic container transfer subsystem and an automated analysis subsystem. In various implementations, the robotic container transfer subsystem is structured and operable to sequentially transfer each of the sample containers from at least one of the sample trays to the automated analysis subsystem, and subsequently transfer each of the sample containers from the automated analysis subsystem back to the respective sample tray. Additionally, in various implementations, the automated analysis subsystem is structured and operable to sequentially receive each sample container from the container transfer subsystem, determine a volume of the object sample within each respective sample container, deposit each object sample within a selected one of a plurality of different size sample cups based on the volume of the respective sample, analyze each respective object sample, and return each object sample to the respective sample container. The system additionally includes a tray shuttle robot structured and operable to distribute and retrieve the sample trays to and from each of the plurality of workstations.

In still other embodiments, the system can include a plurality of workstations structured and operable to analyze a plurality of selected seed samples. In such embodiments, each workstation can include a robotic container transfer subsystem that includes a 3-axis sample container handling robot structured and operable to sequentially remove and replace each of a plurality of sample containers arrayed in at least one sample container tray. Each sample container contains a respective seed sample comprising a plurality of seeds. In various implementations, each workstation can additionally include a bar code scanning module structured and operable to read a bar code affixed to each sample container removed from the respective sample container tray, wherein each bar code provides a unique ID relating to each respective sample container. Still further, each workstation can include an automated analysis subsystem that comprises at least two parallel sample processing assemblies. In various implementations, each sample processing assembly can be structured and operable to determine the volume of each seed sample within each respective sample container that has been removed from the respective tray and placed in the respective sample processing assembly by the sample container handling robot, and then deposit each respective seed sample into a particular one of a plurality of different size sample cups based on the volume of the respective seed sample. In various implementations, each workstation can further include a NIR analysis module structured and operable to NIR scan each seed sample deposited into the sample cups and communicate data acquired by each NIR scan to a master control system. The master control system associates the data with the unique ID of the respective sample container and stores the associated data in a database. The system additionally includes a tray shuttle robot structured and operable to distribute and retrieve the sample trays to and from each of the plurality of workstations.

Further areas of applicability of the present teachings will become apparent from the description provided herein. It should be understood that the description and specific examples are intended for purposes of illustration only and are not intended to limit the scope of the present teachings.

BRIEF DESCRIPTION OF THE DRAWINGS

The drawings described herein are for illustration purposes only and are not intended to limit the scope of the present teachings in any way.

BEST MODE FOR CARRYING OUT THE INVENTION

Figure 1:
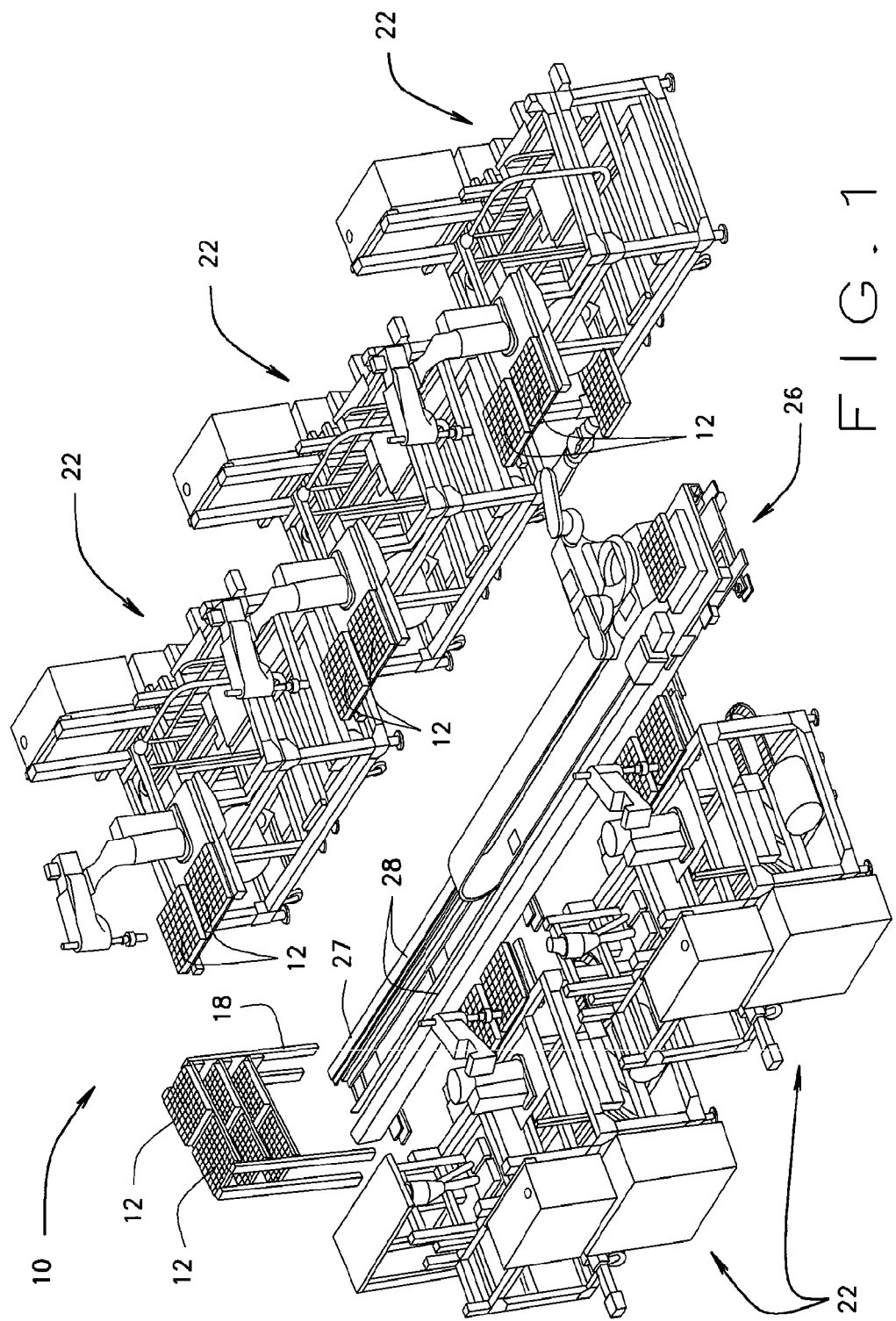
FIG. 1 is an isometric view of a small object analysis system, in accordance with various embodiments of the present disclosure.

The following description is merely exemplary in nature and is in no way intended to limit the present teachings, application, or uses. Throughout this specification, like reference numerals will be used to refer to like elements.

FIG. 1 is an isometric view of a small object analysis system 10 structured and operable to automatically, e.g., utilize robotics, to process a plurality of queued sample trays 12, and analyze a plurality of object samples (not shown) contained within a plurality of sample containers 14 held by each sample tray 12, each object sample comprising a plurality of small objects, such as seeds, or any other suitable small object.

The small object analysis system 10 can be used to determine whether the plurality of object samples possess one or more desired physical, morphological, chemical, and/or genetic traits. Generally, such traits are determined by analyzing the object samples for one or more characteristics indicative of at least one chemical or genetic traits.

Non-limiting examples of characteristics indicative of chemical traits include proteins, oils, carbohydrates, fatty acids, amino acids, biopolymers, pharmaceuticals, starch, fermentable starch, secondary compounds, and metabolites. Accordingly, non-limiting examples of chemical traits include amino acid content, protein content, starch content, fermentation yield, fermentation efficiency, energy yield, oil content, determination of protein profiles determination of fatty acid profiles, determination of metabolite profiles, etc.

Additionally, non-limiting examples of characteristics indicative of genetic traits may include, for example, genetic markers, single nucleotide polymorphisms, simple sequence repeats, restriction fragment length polymorphisms, haplotypes, tag SNPs, alleles of genetic markers, genes, DNA-derived sequences, RNA-derived sequences, promoters, 5' untranslated regions of genes, 3' untranslated regions of genes, microRNA, siRNA, quantitative trait loci (QTL), satellite markers, transgenes, mRNA, ds mRNA, transcriptional profiles, and methylation patterns.

Referring now to FIGS. 1, 2, 3 and 4, in various embodiments, the small object analysis system 10 includes a tray staging console 18, a scalable number of modular workstations 22, and a tray shuttle robot 26. The tray staging console 18 is positioned adjacent a home end 27 of a guide track 28 of the tray shuttle robot 26 and each of the workstations 22 are located adjacent at least one side of the guide track 28. More particularly, the tray staging console 18 and each of the workstations 22 are precisely positioned at a defined tray staging location and a plurality of defined work station locations adjacent the guide track 28 such that shuttle robot 26 can accurately and repeatedly travel along the guide track 28, to shuttle the sample trays 12 between the tray staging console 18 and the workstations 22. Generally, the tray shuttle robot 26 shuttles, or transfers, a plurality of the sample trays 12 populated with a plurality of filled object sample containers 14 between the tray staging console 18 and each of the scalable number of workstations 22. As used herein, the phase 'scalable number of workstations 22' means that the small object analysis system 10 can be configured and reconfigured to include any desirable number of workstations 22.

In various embodiments, the tray staging console 18 can be stationary, such that the sample trays 12 are hand loaded on the staging console 18 prior to shuttling by the shuttle robot 18, and hand unloaded subsequent to shuttling by the shuttle robot 18. In other embodiments, the tray staging console 18 can be mobile and temporarily locked, or fixed, at the tray staging location. Therefore, in such embodiments, the small object analysis system 10 can include a plurality of tray staging consoles 18 that are pre-loaded with a plurality of sample trays 12. Accordingly, each pre-loaded mobile staging console 18 can sequentially be temporarily locked or fixed into place at the tray staging location prior to shuttling of the sample trays 12 by the shuttle robot 18, and then replaced, or exchanged, with a subsequent pre-loaded mobile staging console 18 once each of the sample trays 12 of the previous pre-loaded mobile staging console 18 have been processed, as described below.

Each workstation 22 includes a robotic container transfer subsystem 30, an automated analysis subsystem 34 and a computer based control system 36 that coordinates and controls all the functionality and operations of the respective container transfer subsystem 30 and analysis subsystem 34, i.e., the respective workstation 22. As described in detail below, the robotic container transfer subsystem 30 is structured and operable to sequentially remove, and subsequently replace, each of the sample containers 14 arrayed in at least one of the sample trays 12. And, the automated analysis subsystem 34 is structured and operable to sequentially receive each sample container 14 from the container transfer subsystem 30, remove each object sample from the respective sample container 14, analyze each respective object sample and return each object sample to the respective sample container 14.

It should be understood that the various embodiments of the small object analysis system 10, exemplarily illustrated and described herein, include various braces, beams, platforms, pedestals, stands, etc., to which various components, devices, mechanisms, systems, subsystems, assemblies and sub-assemblies described herein are coupled, connected and/or mounted. Although such braces, beams, platforms, pedestals, stands, etc., are necessary to the construction of various embodiments of the small object analysis system 10, description of their placement, orientation and interconnections are not necessary for one skilled in the art to easily and fully comprehend the structure, function and operation of the various embodiments of the small object analysis system 10. Moreover, such braces, beams, platforms, pedestals, stands, etc., are clearly illustrated in various figures and, as such, their placement, orientation and interconnections are easily understood by one skilled in the art. Therefore, for simplicity, such braces, beams, platforms, pedestals, stands, etc., will be referred to herein merely as system support structures, absent further description of their placement, orientation and interconnections. Additionally, certain figures described and illustrated herein may have portions of the system support structures removed, i.e., not shown, in order to more clearly illustrate the various embodiments of the small object analysis system 10.

Figure 2:
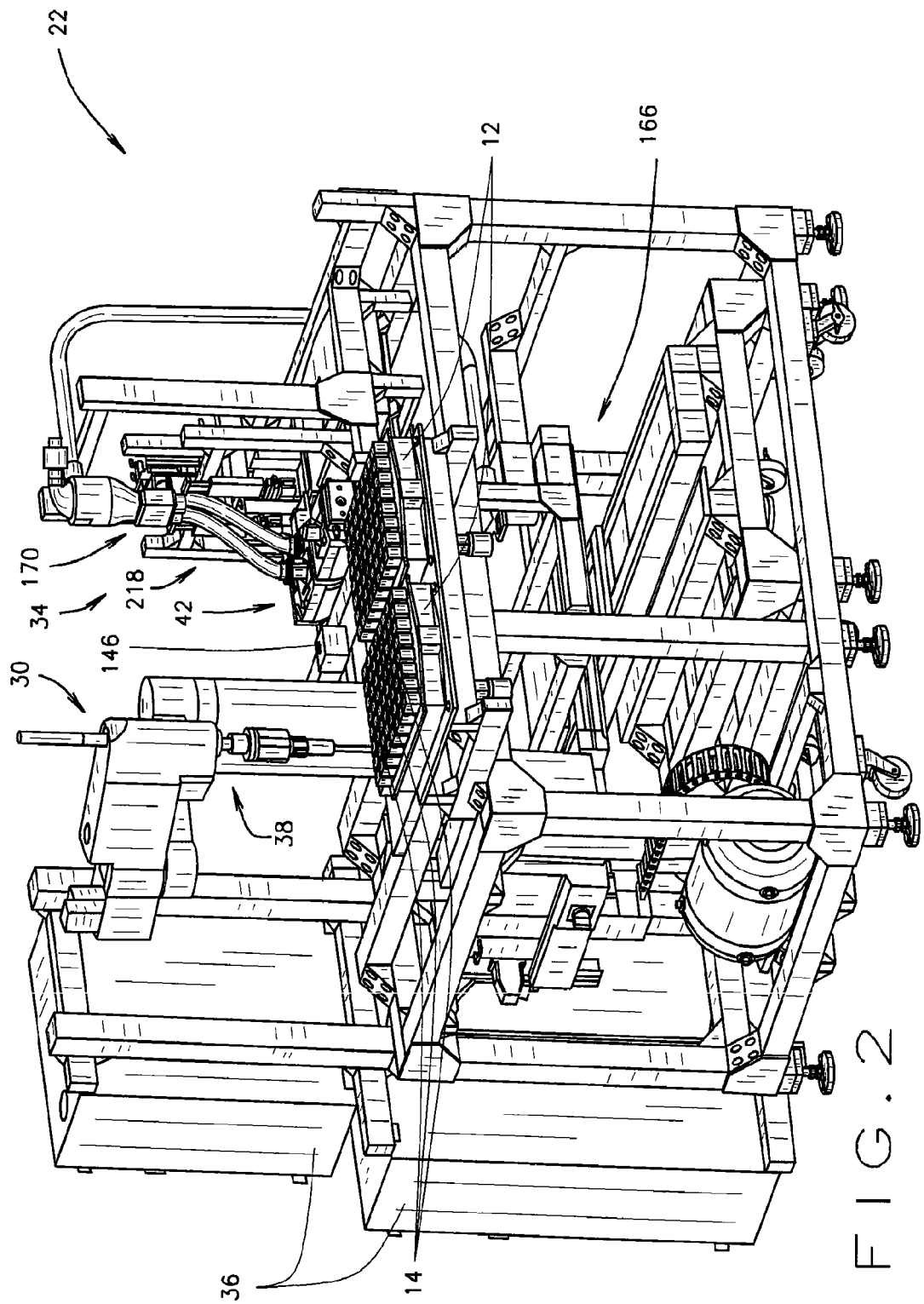
FIG. 2 is an isometric view of one of a plurality of workstations of the small object analysis system shown in FIG. 1, in accordance with various embodiments of the present disclosure.
Figure 3:
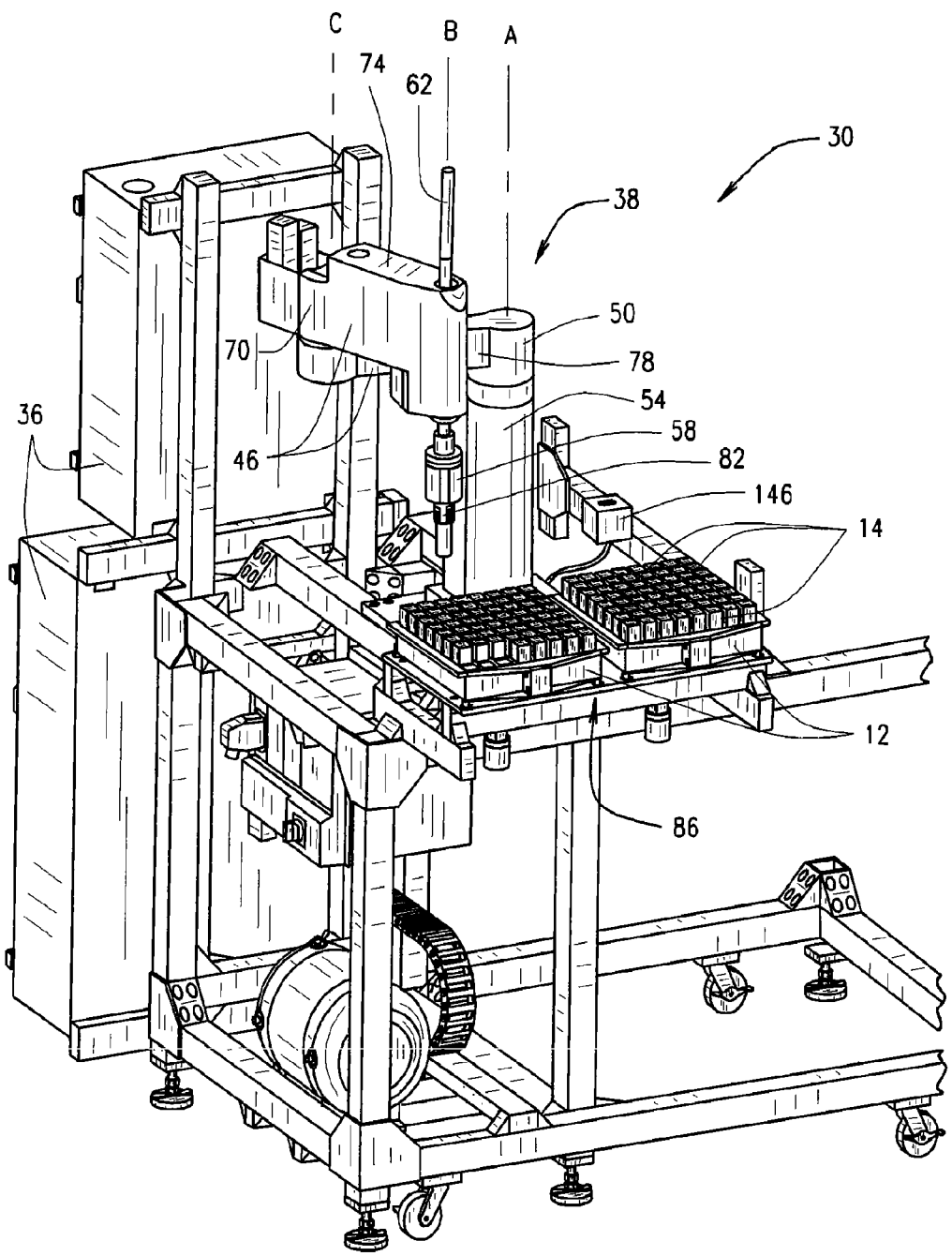
FIG. 3 is an isometric view of a robotic container transfer subsystem included in each of the workstations of the small object analysis system shown in FIGS. 1 and 2, in accordance with various embodiments of the present disclosure.

Referring now to FIGS. 2 and 3, each container transfer subsystem 30 includes a 3-axis sample container handling robot 38 that sequentially removes each individual sample container 14 from the respective sample tray 12 and sequentially places each sample container 14 into one of a plurality of container processing assemblies 42 of the respective analysis subsystem 34. More particularly, the sample container handling robot 38 includes an articulated locating arm 46 pivotally mounted at a proximal end 50 to a main pedestal 54 such that the locating arm 46 is bidirectionally rotatable about a longitudinal axis A of the main pedestal 54, as controlled by the control system 36. The sample container handling robot 38 additionally includes a container grasping device 58 coupled to a distal end of a reciprocating rod 62 that is extendably and rotationally mounted to a distal end 66 of the locating arm 46 such that the container grasping device 58 can be bidirectionally longitudinally moved along an axis B of the reciprocating rod 62 and rotated about the B axis, as controlled by the control system 36. The locating arm 46 is articulated, or jointed, at an elbow 70 such that a forearm portion 74 is pivotal with respect to an aft-arm portion 78 about an axis C at the elbow 70, as controlled by the control system 36.

The container grasping device 58 includes a mechanical grasping claw 82 that is operable to grasp, hold and release selected sample containers 14, as controlled by the control system 36. Thus, once a sample tray 12 has been shuttled from the tray staging console 18 to the container transfer subsystem 30 of the respective workstation 22, the respective control system 36 controls the movement of the 3-axis container handling robot 38 to sequentially remove each of the sample containers 14 from the respective sample tray 12 and transfer each sample container 14 to one of the container processing assemblies 42 of the respective analysis subsystem 34.

Referring to FIGS. 2, 3, 5, 6 and 7, the container transfer subsystem 30 of each workstation 22 further includes a tray queuing platform 86 on which each sample tray 12 is placed by the shuttle robot 26. Generally, each tray queuing platform 86 comprises a docking plate 90 that includes a plurality of foot retention cups 94 recessed within the docking plate 90 for receiving feet 98 extending from the bottom of each sample tray 12. More particularly, when the shuttle robot 26 transfers a sample tray 12 from the staging console 18 to the respective workstation 22, the shuttle robot 26 will place each sample tray 12 on the respective docking plate 90 such that the feet 98 or each sample tray 12 will be positioned within a respective one of the retention cups 94. Therefore, each sample tray 12 will be steadily positioned on the respective docking plate 90 and not easily displaced. Additionally, placing the sample trays 14 on the docking plates 90 with the tray feet 98 positioned within the retention cups 94, will position each sample tray 12 on the respective docking plate 90 in a desired location and orientation. More particularly, each sample tray 12 will be located and oriented on the respective docking plate 90 so that a location of each of a plurality of container wells 102 in each sample tray 12, and more particularly the location of each sample container 14, with respect to the queuing platform 86 and docking plate 90 will be known to the respective control system 36.

For example, in various implementations, each docking plate 90 can lie within an X-Y plane of a rectangular coordinate system. Therefore, once each sample tray 12 is placed on the respective docking plate 90, with tray feet 98 within the respective retention cups 94, an (X,Y) coordinate location of each container well 102, and sample container 14, will be known to the respective control system 36. Accordingly, the sample container handling robot 38 can be operated by the respective control system 36 to remove, and subsequently replace, each sample container 14 from each respective sample tray 12.

Additionally, to accurately and consistently locate the sample trays 12 on the queuing platforms 86, in various embodiments, each of respective docking plates 90 include a plurality of tray locating fixture first halves 106 that engage and/or mate with a plurality of locating fixture second halves 110 associated with, i.e., formed with or connected to, the bottom of each sample tray 12. The tray locating fixture first and second halves 106 and 110 engage and/or mate with each other as the shuttle robot 26 places each respective sample tray 12 on the respective docking plate 90 to substantially precisely locate and orient each respective sample tray 12 on the respective docking plate 90. Accordingly, each sample tray 12 will be accurately and repeatably located and oriented on the respective docking plate 90 in a precise manner. Moreover, accurately and repeatably locating each sample tray 12 on the respective docking plate 90, accurately and repeatably locates each of the container wells 102 and respective sample containers 14 at known locations with respect to the docking plate 90 programmed into the control system 36. Therefore, the location of each respective sample container 14 is coordinated with the operation of the sample container handing robot 38 such that each sample container 14 can be removed from each respective sample tray 12, transferred to the analysis subsystem 34 and returned to the container transfer subsystem 30, as described herein.

The tray locating fixture first and second halves 106 and 110 can be any engageable and/or mateable fixtures, connectors, components, etc., that are suitable to substantially precisely locate and orient each respective sample tray 12 on the respective docking plate 90. For example, in various embodiments, the tray locating fixture first halves 106 can be locating recesses 106 within a top surface 114 and the locating fixture second halves 110 can be locating pins 110 that engage and/or mate with the locating recesses 106 to substantially precisely locate and orient each respective sample tray 12 on the respective docking plate 90. In various implementations, the locating recesses 106 can have a V-shaped convexity and the locating pins 110 can have a rounded tip. Thus, in such implementations, as each respective sample tray 12 is placed on the respective docking plate 90, the rounded tip of each locating pin 110 will slidingly engage any portion of the respective locating recess 106 and the V-shaped convexity will 'guide' and 'center' the locating pins 110 within each respective locating recess 106, thereby substantially precisely locating and orienting each respective sample tray 12 on the respective docking plate 90.

Furthermore, in various embodiments, each sample tray queuing platform 86 comprises a tray locking mechanism first half 118 for each sample tray the respective queuing platform 86 is structured to support. Additionally, a bottom plate 120 of each sample tray 12 includes a tray locking mechanism second half 122 that is engageable with a respective tray locking mechanism first half 118 to steadily and securely retain each sample tray 12 on the respective docking plate 90. The tray locking mechanism first and second halves 118 and 122 can be any engageable and/or interlocking mechanisms, fixtures, connectors, components, etc., that are suitable to steadily and securely retain each sample tray 12 on the respective docking plate 90. For example, in various embodiments, each tray locking mechanism first half 118 can comprise a T-shaped key or latch 118 and the tray locking mechanism second half 122 can be a C-shaped bracket 122 (or a pair of L-shaped brackets) that can be engaged by the T-shaped key 118 to steadily and securely retain each sample tray 12 on the respective docking plate 90.

Further yet, in various embodiments, each T-shaped key 118 can be coupled to a linear and rotary actuator 126 operable to extend, retract and rotate the respective T-shaped keys 118, as controlled by the respective control system 36. For example, prior to a sample tray 12 being placed on the respective docking plate 90, the control system 36 can command each actuator 126 to retract the respective T-shaped key 118 within an orifice, or an intention, 130. Subsequently, once a sample tray 12 is located and oriented on the respective docking plate 90, as described above, the control system 36 can command the respective actuator 126 to extend the respective T-shaped key 118 such that the T-shaped key 118 passes through a mouth 134 of the respective C-shaped bracket 122. The control system 36 can then command the actuator 126 to rotate the T-shaped key 118 such that wings 138 of the T-shaped key 118 align collinearly with fingers 142 of the C-shaped bracket 122. Thereafter, the control system 36 can command the actuator 126 to retract the T-shaped key 118 such that the wings 138 of the T-shaped key 118 engage the fingers 142 of the C-shaped bracket 122 to apply a downward force, i.e., a force toward the top 114 of the respective docking plate 90. The downward force will firmly engage the feet 98 of the respective sample tray 12 within the corresponding retention cups 94, and, in various embodiments, firmly engage the tray locating fixture first halves 106 with the second halves 110, such that the respective sample tray 12 can not be removed from the docking plate 90 or displaced, dislodged, relocated or reoriented from the desired location and orientation on the respective docking plate 90.

Figure 8:
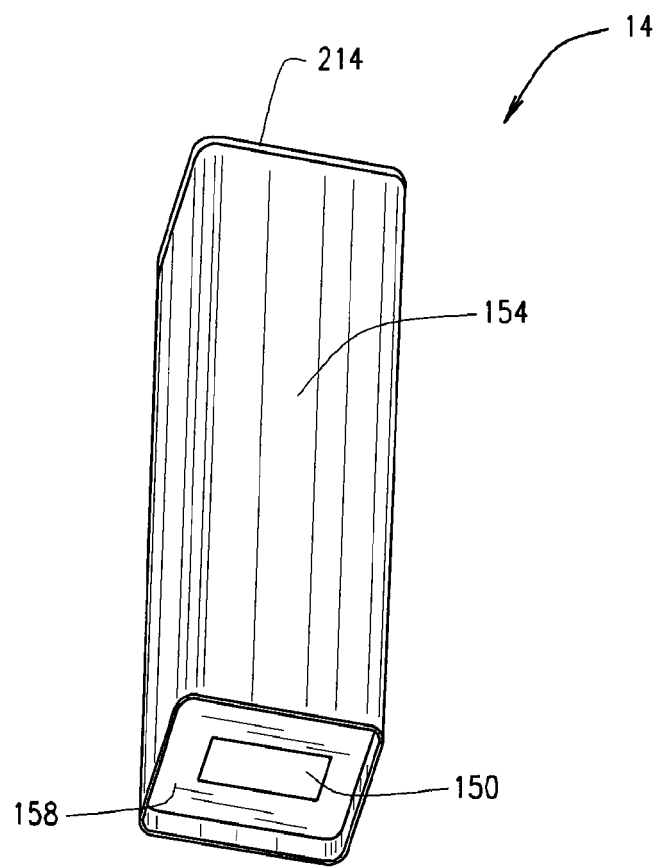
FIG. 8 is an isometric view of a small object sample container structured to retain a plurality of small objects analyzed by the small object analysis system shown in FIG. 1, in accordance with various embodiments of the present disclosure.

Referring now to FIGS. 2, 3 and 8, in various embodiments, each container transfer subsystem 30 can further include an identification device reader 146. Each identification device reader 146 is communicatively connected to the respective control system 36 to read a sample identification device 150 associated with each sample container 14. In various implementations, the respective control system 36 can control the sample container handling robot 38 such that each sample container 14 is at least momentarily positioned adjacent the respective identification device reader 146 as the sample container handling robot 38 moves each sample container 14 from the respective sample tray 12 to a container processing assembly 42 of the analysis subsystem 34 of the respective workstation 22. Each identification device 150 provides unique identification information, i.e., data, relating to each respective sample container 14 and/or information, i.e., data, regarding the small object sample disposed within the respective sample container 14.

As each sample container 14 is placed adjacent the identification device reader 146, the reader 146 interprets, e.g., reads, views, senses, scans, etc., the respective identification device 150 and the control system 36 stores the information provided as one or more electronic databases, spreadsheets and/or look-up tables of the respective control system 36. In various embodiments, the one or more electronic databases, spreadsheets and/or look-up tables can be stored locally at the respective control system 36. Alternatively, the information can be stored remotely, e.g., on a remote server network or a secure Internet site, as one or more electronic databases, spreadsheets and/or look-up tables.

In various embodiments, each information device 150 can be a 'bar code' label and the identification device reader 146 can be a bar code reader. Thus, as the container handling robot 38 moves each sample container 14 from the respective sample tray 12 to one of the container processing assemblies 42 each sample container 14 is passed, or moved, adjacent the bar code reader 146 to scan the respective bar code information device 150. The read information is subsequently stored on an electronic storage device or other computer readable media in a desired format, e.g., an electronic database, spreadsheet and/or look-up table. In various other embodiments, each identification device 150 can comprise any other sort of 'readable' label and the identification device reader 146 can comprise any suitable corresponding automated label reader. For example, each identification device 150 can comprise a magnetic tag or a magnetic strip readable by a suitable magnetic tag or strip reader 146. Alternatively, each identification device 150 can comprise an electronic tag or device readable by a suitable electronic tag or device reader 146.

With further reference to FIG. 8, in various embodiments, a central housing 154 of each sample container 14 is fabricated from a transparent material, or alternatively a translucent material, such that the small objects disposed therein are visible. Additionally, in various embodiments, the identification device 150 of each sample container 14 is located on a bottom 158 of each respective sample container 14. Therefore, as each sample container 14 is moved from the respective sample tray 12 to one of the container processing assemblies 42, the container handling robot 38 passes the bottom of each sample container 14 adjacent the identification device reader 146 to obtain the unique identification information, i.e., data, relating to each respective sample container 14 and/or information, i.e., data, regarding the small object sample disposed within the respective sample container 14. Furthermore, in various embodiments, the bottom plate 120 of each sample tray 12 includes a plurality of openings, or windows, 158, wherein each opening 158 corresponds to and aligns with a respective one of the wells 102. Thus, the bottom 158 of each sample container 14 arrayed in the respective sample tray 12, and in various implementations, the associated identification device 150, can be viewed through the respective opening 158.

Thus, operation of the container transfer subsystem 30 comprises precisely locating and orienting the sample tray 12 on the docking plate of a workstation 22, via the locating fixture first and second halves 106 and 110, as the shuttle robot 26 places the sample tray 12 on the respective docking plate 90. In various embodiments, the respective control system 36 then commands the tray locking mechanism first half 118 to engage the tray locking mechanism second half 122 to steadily and securely retain the sample tray 12 on the respective docking plate 90. The control system 36 then commands the sample container robot 38 to position the container grasping device 58 above a target, or desired, sample container 14 to be removed. Once the container grasping device 58 is in position above the target sample container 14, the control system 36 opens the mechanical grasping claw 82 and translates the reciprocating rod 62 downward along the B axis to lower the grasping claw 82 around the target sample container 14. The grasping claw 82 is then closed to grasp the sample container 14 and the reciprocating rod 62 is translated upward along the B axis to remove the sample container 14 from the sample tray 12. The control system 36 then commands the sample container robot 38 to move the sample container past the identification device reader 146, whereby the respective identification device 150 is interpreted, or read, and the corresponding information, i.e., data, is stored as one or more electronic databases, spreadsheets and/or look-up tables of the respective control system 36. Subsequently, the sample container robot 38 is commanded to deposit the sample container 14 into one of the container processing assemblies 42. In various embodiments, once the identification device 150 of a respective sample container 14 has been read, the control system 36 determines whether the data provided by the respective identification device 150 is valid, i.e., interpretable by the control system 36. If the identification device 150 is valid, the sample container robot 38 transfers the sample container 14 to one of the container processing assemblies 42. However, if the identification device 150 is determined to be invalid, the sample container robot 38 is commanded to return the respective sample container 14 to the sample tray 12, and proceed with removing, scanning and transferring or returning a subsequent target sample container 14.

Figure 4:
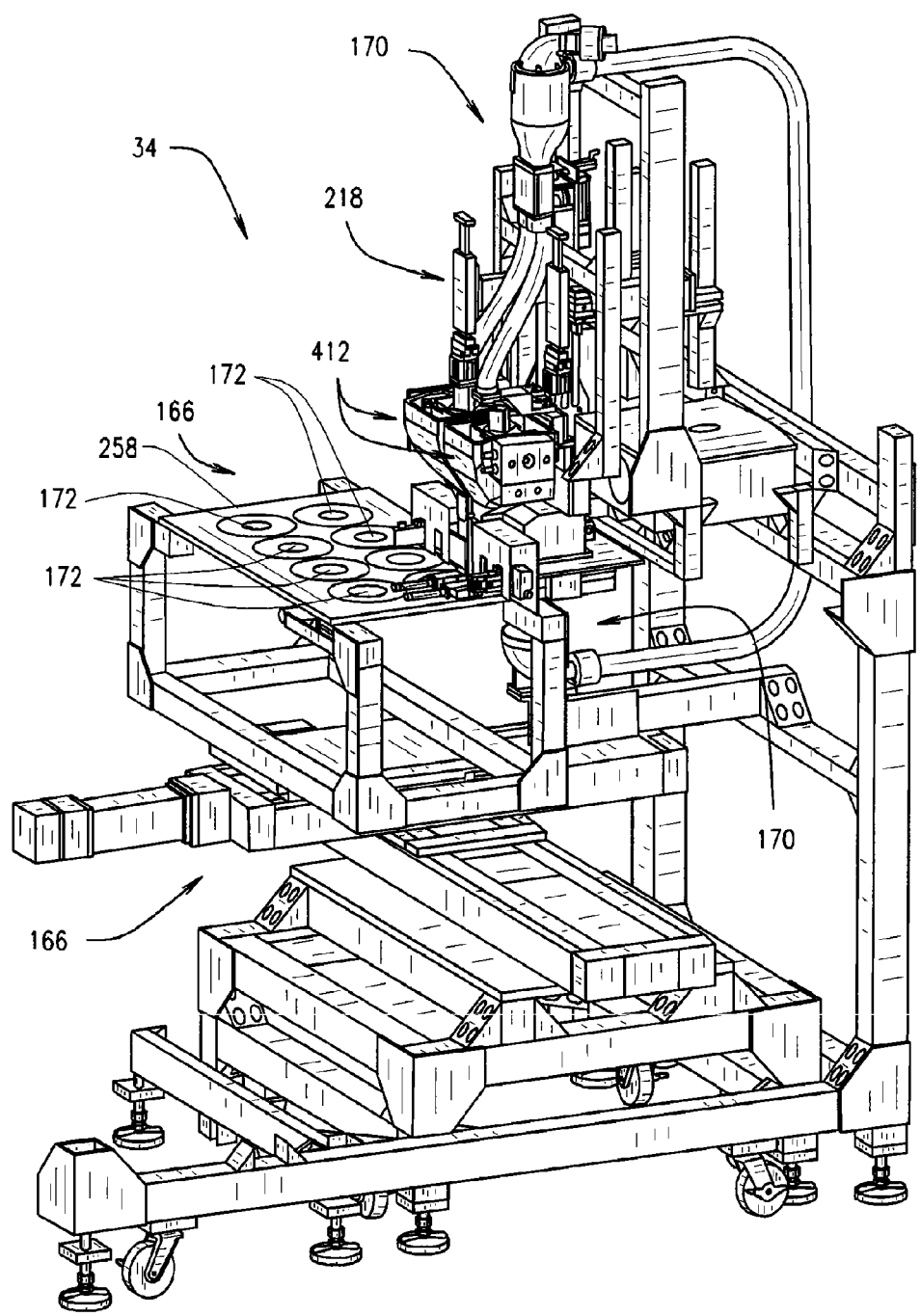
FIG. 4 is an isometric view of an automated analysis subsystem included in each of the workstations of the small object analysis system shown in FIGS. 1 and 2, in accordance with various embodiments of the present disclosure.
Figure 5:
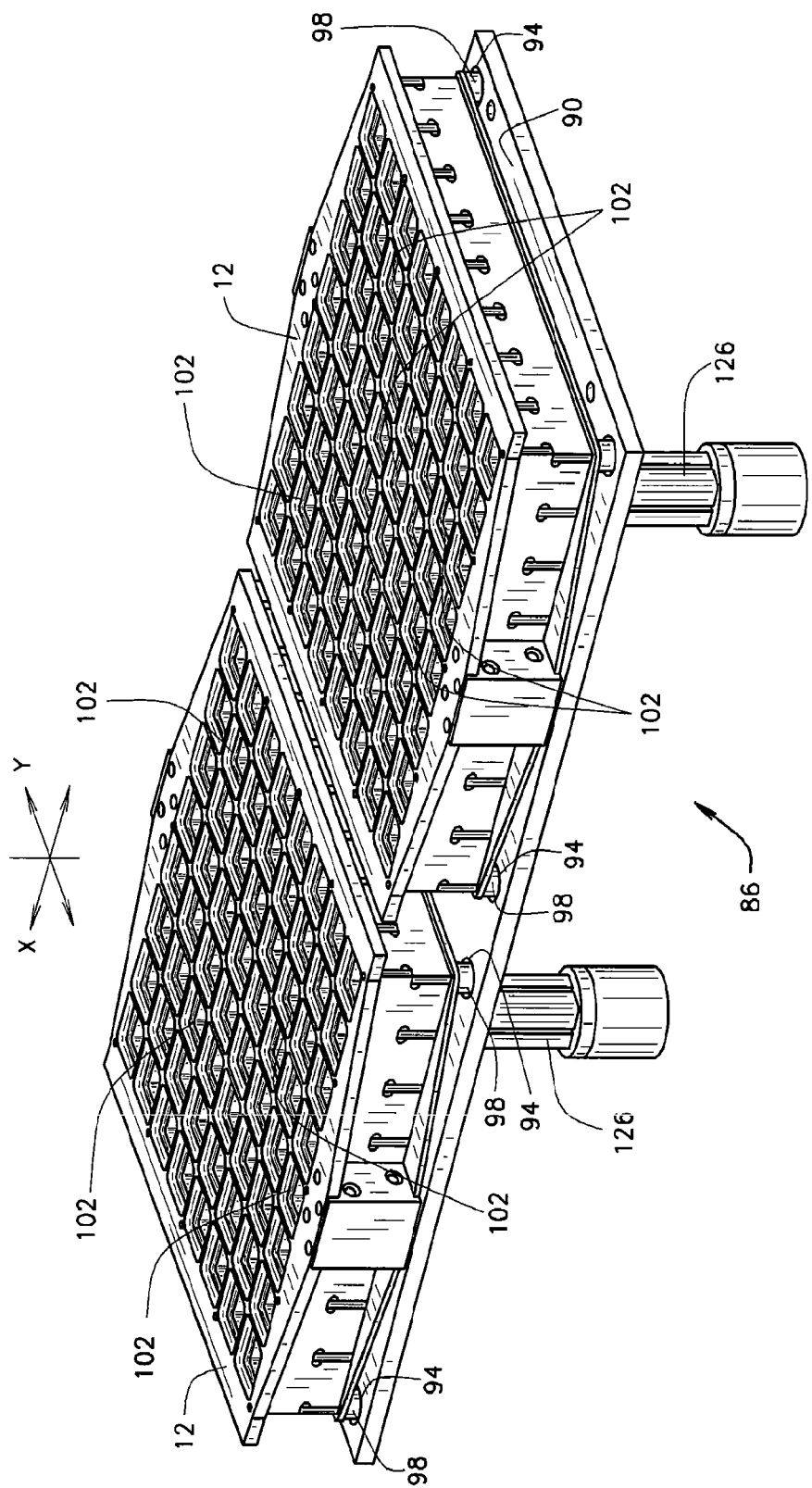
FIG. 5 is an isometric view of a queuing platform of the robotic container transfer subsystem, shown in FIG. 3, having a plurality of sample trays positioned thereon, in accordance with various embodiments of the present disclosure.
Figure 6:
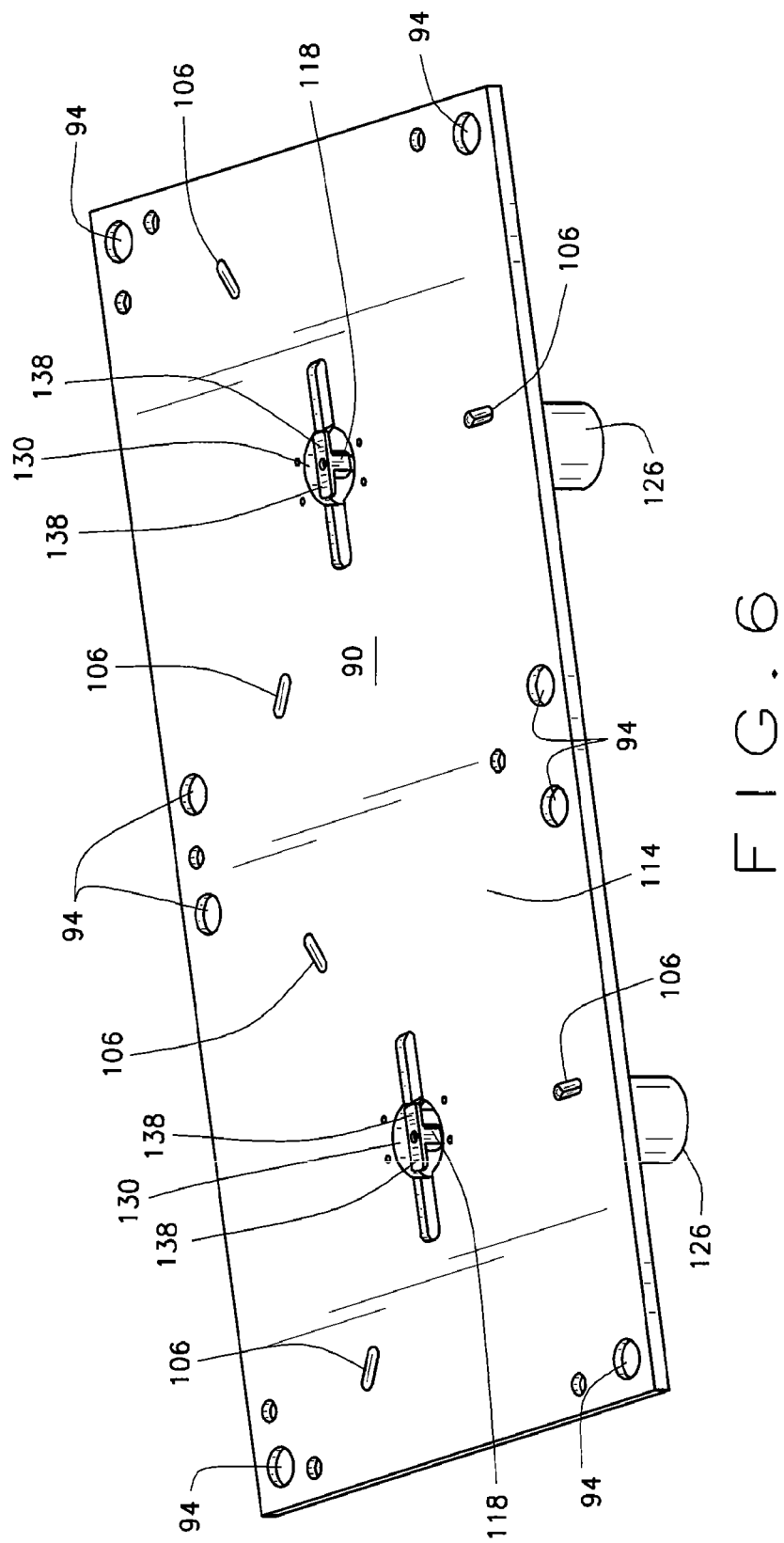
FIG. 6 is an isometric top view of the queuing platform shown in FIG. 5, in accordance with various embodiments of the present disclosure.
Figure 7:
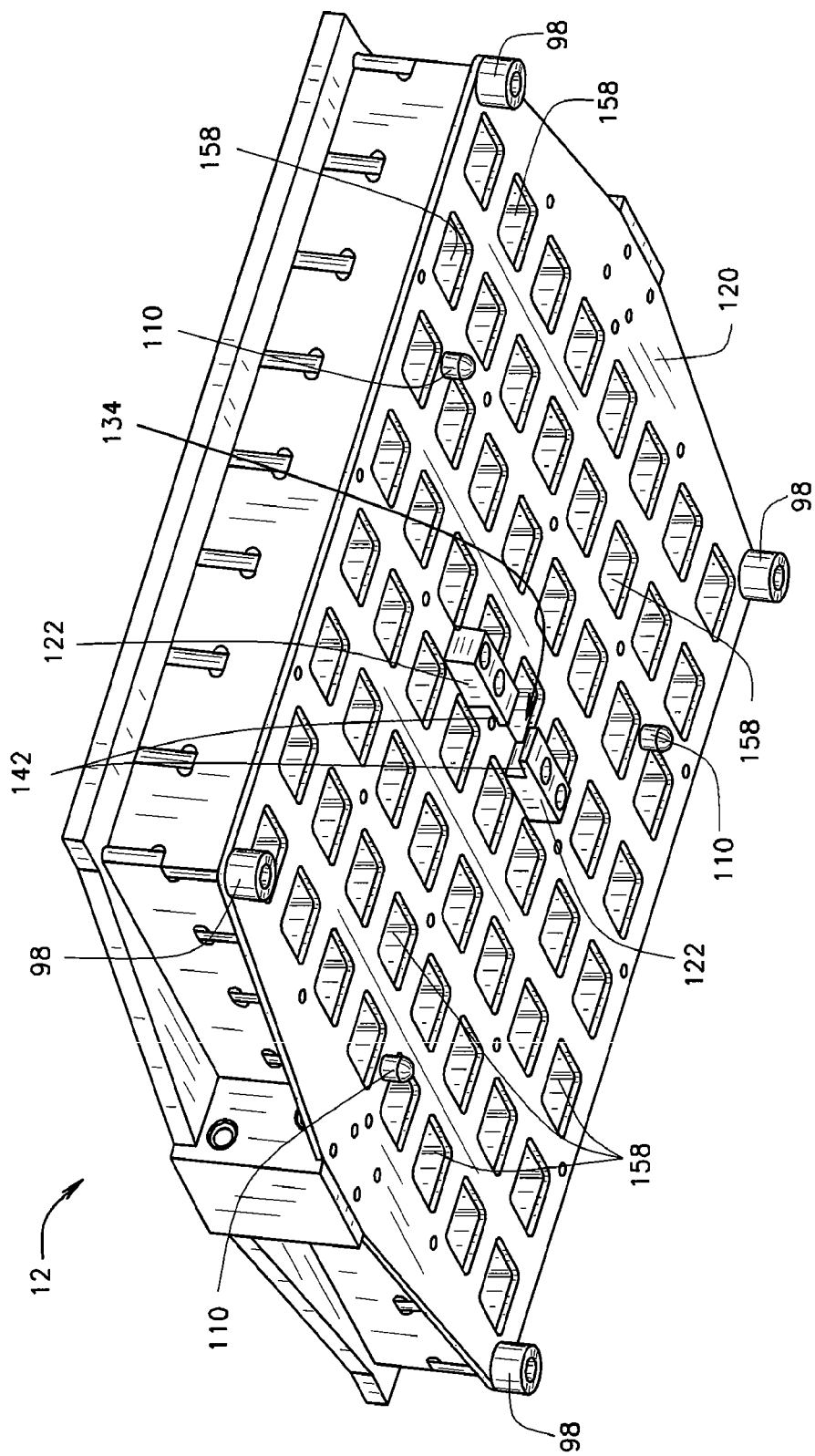
FIG. 7 is an isometric bottom view of a sample tray, shown in FIG. 5, in accordance with various embodiments of the present disclosure.

Referring now to FIGS. 2 and 4, as described above, the automated analysis subsystem 34 is structured and operable to sequentially receive each sample container 14 from the container transfer subsystem 30, remove each object sample from respective sample container 14, analyze each respective object sample and return each object sample to the respective sample container 14. Generally, the analysis subsystem 34 includes the plurality of container processing assemblies 42, a data collection assembly 166 and an object return assembly 170.

Referring now to FIGS. 2, 4, 9 and 10, as also described above, each automated analysis subsystem 34 includes at least one processing assembly 42. Generally, each container processing assembly 42 is structured and operable to receive selected sample containers 14 removed from the respective sample tray 12 by the 3-axis sample container handling robot 38 of the container transfer subsystem 30, obtain data to determine a volume of the object sample contained within each respective sample container 14, and deposit each measured object sample into one of a plurality of data acquisition cups 172 of the respective data collection assembly 166. In various embodiments, each container processing assembly 42 includes an object dispensing module 174 coupled to a height measurement module 178. The object dispensing module 174 is structured and operable to retain each sample container 14 placed therein by the container handling robot 38 and dispense the objects from the respective sample containers 14 into the height measurement module 178. The height measurement module 178 is structured and operable to obtain data to determine a volume of the object sample contained within each respective sample container 14.

More particularly, the object dispensing module 174 includes a container retention block 182 rotatably mounted within a dispensing funnel 186. That is, the object dispensing module 174 includes a rotary motor 190 that is controlled by the respective control system 36 and includes a shaft 194 to which the respective container retention block 182 is connected. Additionally, each container retention block 182 includes a retention bay 198 structured to receive and retain each sample container 14 placed therein by the container handling robot 38. Each retention bay 198 is sized such that each respective sample container 14 is steadily supported therein but yet can be easily inserted and removed therefrom by the container handling robot 38. Each container retention block 182 additionally includes a container clamping mechanism 202 that is controlled by the respective control system 36 to move between an 'Opened' position wherein each respective sample container 14 is permitted to be inserted and removed from the respective retention bay 198, and a 'Closed' position wherein each respective sample container 14 is securely retained within the respective retention bay 198. Thus, prior to a sample container 14 being inserted into the retention bay 198 of a container retention block 182, as controlled by the respective control system 36, the respective container clamping mechanism 202 is placed in the 'Opened' position, and then moved to the 'Closed' position once the sample container 14 has been inserted into retention bay 198. Accordingly, the sample container 14 is firmly retained within the respective retention bay 198.

In various embodiments, the container clamping mechanism 202 includes an actuator 206 that, via control of the respective control system 36, affects the movement of one or more clamping feet 210 to gently squeeze, or grasp, and release the sample container 14 disposed within the respective retention bay 198. Thus, to retain the sample container 14 within the respective retention bay 198, the control system 36 commands the actuator 206 to move the clamping feet 210 to the 'Closed' position wherein the clamping feet 210 gently squeeze, or grasp, the sample container 14 such that the sample container 14 is affirmatively retained within the respective retention bay 198. Contrarily, to insert or remove a sample container 14 to or from the respective retention bay 198, the control system 36 commands the actuator 206 to move the clamping feet 210 to the 'Opened' position wherein the clamping feet 210 are moved to a position that allows a sample container 14 to be easily placed into or extracted from the respective retention bay 198.

Referring now to FIGS. 2, 4, 8, 9, 10 and 11, in various implementations, each sample container 14 includes a cap 214 fitted on a top portion of each respective sample container 14. To remove the cap 214 from each sample container 14 placed in the container retention block 182 of one of the processing assemblies 42, in various embodiments, each analysis subsystem 34 further includes at least one container cap handling assembly 218 for each container processing assembly 42. Each cap handling assembly 218 includes a cap grasping device 222 mounted to a first linear actuator 226 that is controllable by the respective control system 36 to selectively raise and lower the respective cap grasping device 222. Each first linear actuator 226 is mounted to a second linear actuator 230 that is controllable by the respective control system 36 to selectively move the respective cap grasping device 222 between an 'Extended' position and a 'Retracted' position. When in the 'Extended' position, the respective cap grasping device 222 is positioned directly above a sample container 14 retained with a respective retention bay 198. Contrarily, when in the 'Retracted' position, the respective cap grasping device 222 is moved to a position away from and non-obstructing to an area directly above the respective processing assembly 42.

Each cap grasping device 222 includes a mechanical clasping claw 234 that is operable to grasp, hold and release the cap 214 of each respective sample container 14, as controlled by the respective control system 36. Thus, prior to the container handling robot 38 placing a sample container 14 into one of the container processing assemblies 42, the respective control system 36 places the second actuator 230 of the corresponding cap handling assembly 218 in the 'Retracted' position. Once the sample container 14 has been inserted into the retention bay 198 of the respective container retention block 182 and securely retained therein by the respective container gripping mechanism 202, the respective control system 36 moves the second linear actuator 230 from the 'Retracted' position to the 'Extended' position to locate the cap clasping claw 234 of the respective cap grasping device 222 directly above the sample container 14. The control system 36 then operates the cap handling assembly first actuator 226 to lower the respective cap grasping device 222 such that the respective cap clasping claw 234 enclosed the cap 214 of the sample container 14. Subsequently, the control system 36 closes the cap clasping claw 234 to grasp the cap 214 and raises the first actuator 226 and hence, the cap grasping device 222, to remove the cap 214 from the sample container 14. The second actuator 230 is then moved to the 'Retracted' position to temporarily store the container cap 214 as the sample within the respective sample container 14 is processed and analyzed, as described further below.

Figure 10:
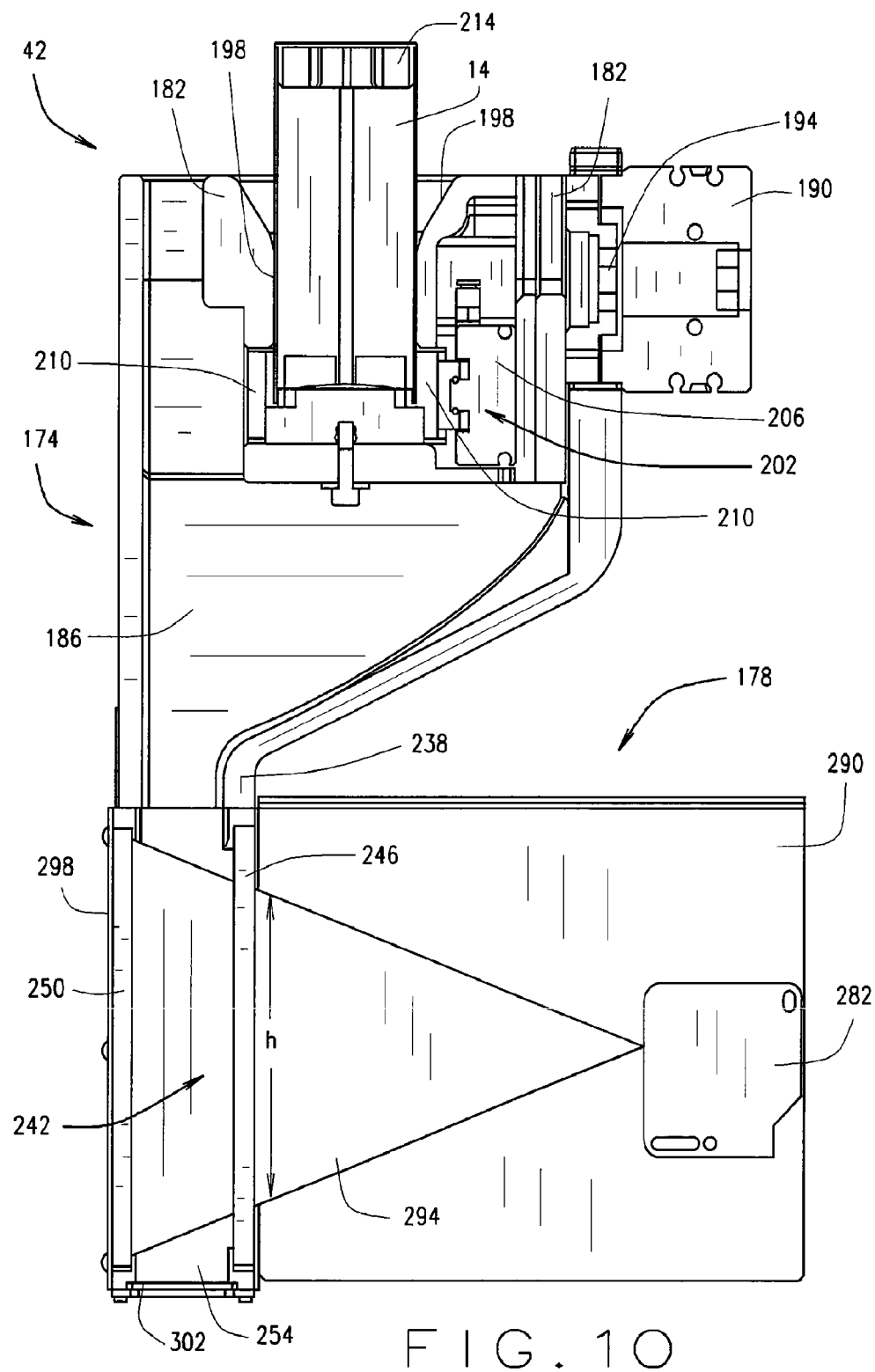
FIG. 10 is a cross-sectional view along line M-M of the processing assembly shown in FIG. 9, in accordance with various embodiments of the present disclosure.
Figure 11:
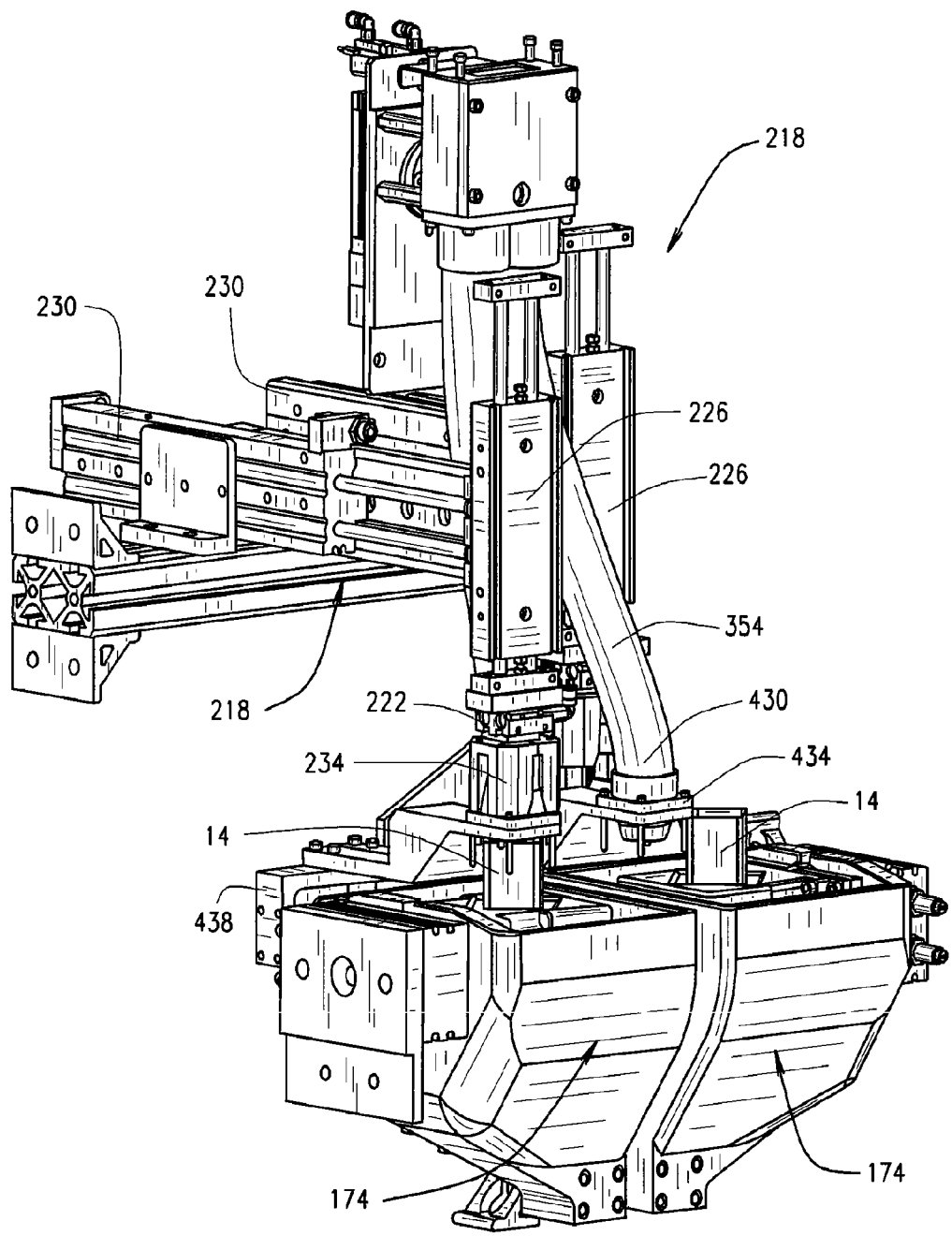
FIG. 11 is an isometric view of a container cap handling assembly of the automated analysis subsystem shown in FIG. 4, in accordance with various embodiments of the present disclosure.

Referring now to FIGS. 10 and 11, the height measurement module 178 is coupled to the object dispensing module 174 at an outlet end 238 of the dispensing funnel 186. More particularly, the height measurement module 178 includes a measuring chamber 242 that is coupled to the outlet end 238 of the dispensing funnel 186. Once a sample container 14 has been placed into the retention block retention bay 198 of an object dispensing module 174 and retained therein by the respective container gripping mechanism 202 (and the cap 214 has been removed in the embodiments wherein each sample container 14 includes a cap 214), the respective control system 36 actuates the rotary motor 190 to rotate the respective container retention block 182 one-hundred-eighty degrees) (180°). Rotating the container retention block 182 180° dispenses the object sample disposed within the respective sample container 14 into the respective dispensing funnel 186. Subsequently, the dispensed object sample is funneled into the respective measuring chamber 242.

The measuring chamber 242 includes a front wall 246, a back wall 250 and a pair of side walls 254 that define an interior space having a particular predetermined cross-sectional area. The height measuring module 178 further includes a height measuring device 282. As described above, the height measurement module 178 is structured and operable to obtain data to determine a volume of the object sample contained within each sample container 14. To obtain the volumetric data of each object sample, the height measurement device 282 is operable to measure a height of each respective object sample once each sample is dispensed into the measuring chamber 242. The measured height of each sample within the measuring chamber 242 is utilized by the respective control system 36, along with the known predetermined cross-sectional area of the measuring chamber 242, to calculate a volume of each respective object sample.

The height measurement device 282 can be any device suitable to measure the height of each respective object sample once each sample is dispensed into the measuring chamber 242. For example, in various embodiments, the height measurement device 282 can be an optical device and sensor that emits a field of light 294 projected onto each sample dispensed into the measuring chamber 242. In such embodiments, the measuring chamber front and back walls 246 and 250 can be fabricated of transparent material, or compound, such quartz and the measuring chamber 242 can include a reflector strip 298 located adjacent, or affixed to, an exterior side of the transparent back wall 250. Additionally, the optical height measuring device and sensor 282 can be calibrated to emit the light field 294 such that the projected light field 294 has height h that is greater than the height of each object sample within the measuring chamber 242. Therefore, the portion of the emitted field of light 294 that is not projected onto the respective object sample within the measuring chamber 242, i.e., the portion of the light field 294 that is not blocked by the respective object sample, will reflect off of the reflector strip 298 and be sensed by the optical height measuring device and sensor 282. The optical height measuring device and sensor 282 reads, or measures, the amount of reflected, or returned, light to determine the height of the object sample within the measuring chamber 242. Then utilizing the measured height of the object sample and the known cross-sectional area of the measuring chamber 242, the respective control system 36 can calculate the volume of each respective object sample.

Alternatively, the height measurement device 282 can be any other device suitable to measure the height of each respective object sample once each sample is dispensed into the measuring chamber 242. For example, in various embodiments, the height measuring device 282 can be a magnetic resonance imaging (MRI) device, or an X-ray device, or a computed tomography (CT) device, or a weight measurement device wherein the weight of the respective object sample and the known cross-sectional area of the measuring chamber 242 are used to calculate the volume of the respective sample, etc.

In various embodiments, the height measuring module 178 can further include a linear actuator 286 to which the height measuring device 282 mounted. In such embodiments, the linear actuator 286 is controlled by the respective control system 36 to move the height measuring device 282 laterally within a housing 290 of the height measuring module 178, in the F$^+$ and the F$^-$ directions. Therefore, the height measuring device 282 can be moved laterally within the housing 290 as the height measuring device 282 is collecting height data. Therefore, more height data can be collected for each sample to more accurately calculate the respective volume. For example, in the embodiments wherein the height measuring device 282 is an optical device and sensor, the projected field of light 294 can be scanned across the width of each respective object sample dispensed into the measuring chamber 242, via the actuator 286. Therefore, more height data can be collected to more accurately calculate the height and volume of each respective object sample.

Figure 9:
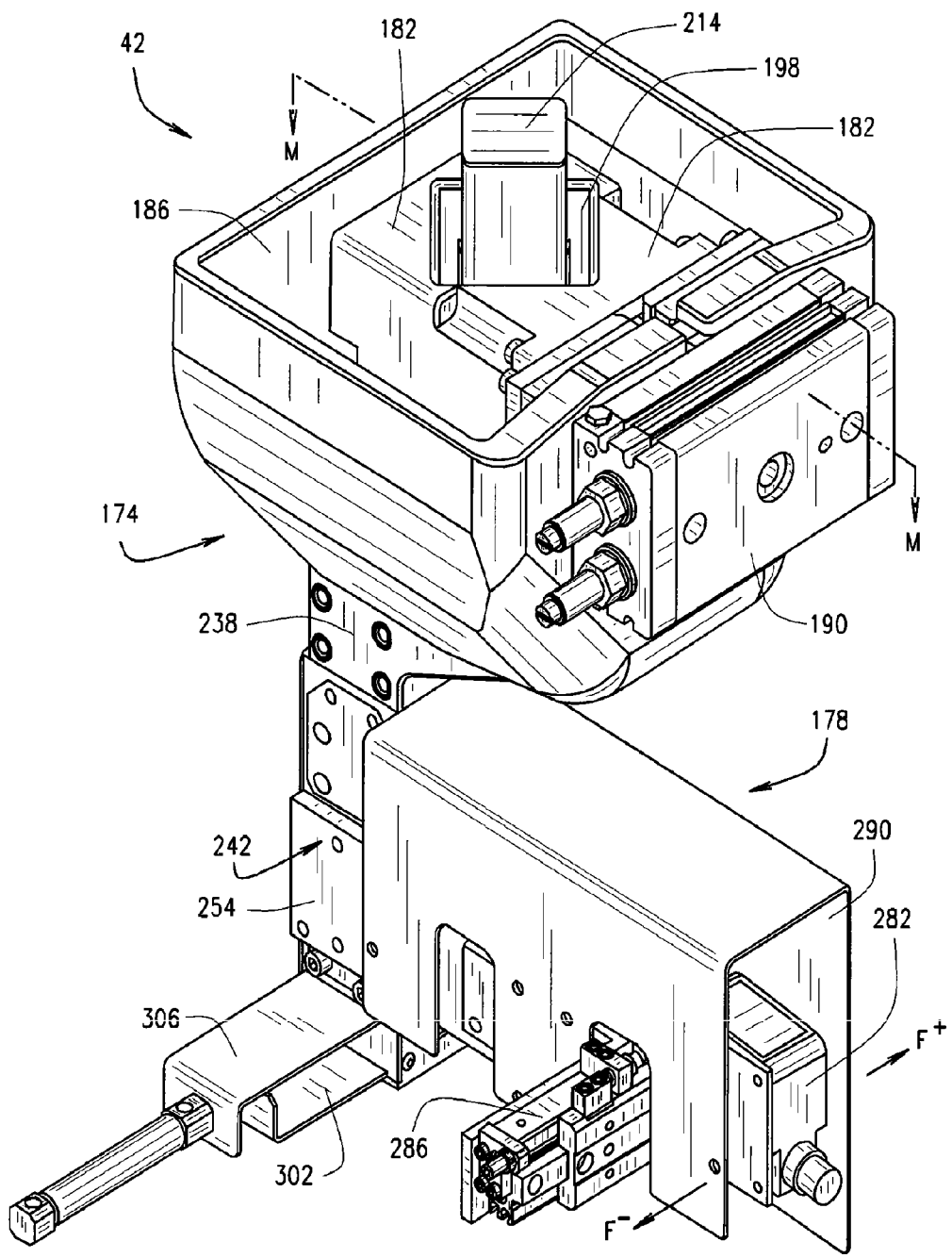
FIG. 9 is an isometric view of a processing assembly included in the automated analysis subsystem, shown in FIG. 4, in accordance with various embodiments of the present disclosure.

With further reference to FIGS. 9 and 10, the height measuring module 178 additionally includes a retractable bottom plate 302 slideably connected to a bottom of the measuring chamber 242 and a linear actuator 306 operable, as controlled by the respective control system 36, to move the bottom plate 302 between a 'Closed' position and an 'Opened' position. In the 'Closed' position, an object sample deposited into the measuring chamber 242 is retained therein while the volume of the respective sample is being calculated, as described above. Once the volume of an object sample has been calculated, the respective control system 36 will command the actuator 306 to retract the bottom plate 302 to the 'Opened' position such that the object sample is dispensed from the measuring chamber 242 into a selected data acquisition cup 172 of the respective data collection assembly 166, as described below.

Referring now to FIGS. 4, 9, 12 and 13, as described above, in various embodiments, each analysis subsystem 34 includes the data collection assembly 166. Generally, each data collection assembly 166 is structured and operable to analyze each respective object sample processed by the respective workstation 22, e.g., determine characteristics relating to various physical, morphological, chemical and/or genetic traits of the objects within sample.

In various implementations, each data collection assembly 166 includes a data collection instrument 256 and a presentation tray 258 mounted to a presentation tray cage 260 that is mounted to a respective X-Y translation stage 262. The presentation tray 258 includes a plurality of different sized data acquisition cups 172. More particularly, each data acquisition cup 172 has a depth that is substantially equal to the depth of each of the other data acquisition cups 172, but has a different diameter d than the diameter d of each of the other data acquisition cups 172. Thus, each data acquisition cup 172 of each respective presentation tray 258 has a different size diameter and a corresponding different interior volume to accommodate the different volumes of the object samples, as described below.

The X-Y stage 262 is a two-dimensional translation mechanism, including an X axis translating track 264 and a Y axis translating track 266. The X-Y stage 262 additionally includes a first linear actuator 268 operable to bidirectionally move a first carriage 270 along the length of the X axis translating track 264, as controlled by the respective control system 36. The X-Y stage 262 further includes a second linear actuator 272 operable to bidirectionally move a second carriage 274 along the length of the Y axis translating track 266, as controlled by the respective control system 36. The Y axis translating track 266 is mounted to the first carriage 270 and a presentation tray cage 260 is mounted to the second carriage 274.

Each data collection instrument 256 is mounted to stationary system support structure such that each data collection instrument 256 remains at a constant location within the respective analysis subsystem 34. Similarly, each respective height measurement module 178 is mounted to stationary system support structure such that each respective measuring chamber 242 remains at a constant location within the respective analysis subsystem 34. However, the presentation tray 258 is movable in two dimensions. Therefore, in operation, each control system 36 can control the respective first and second actuators 268 and 272 to move the respective presentation tray cage 260 within an X-Y coordinate system to precisely position selected ones of the respective data acquisition cups 172 beneath the respective stationary measuring chamber 242 and stationary data collection instrument 256.

More specifically, based on the calculated volume of a particular object sample retained within the respective measuring chamber 242, the respective control system 36 will map the object sample to a particular 'target' data acquisition cup 172 having a particular volume corresponding to the calculated object sample volume. Once a respective object sample has been mapped to a target data acquisition cup 172, the control system 36 operates the X-Y stage 262 to move the target data acquisition cup 172 beneath the respective measuring chamber 242. The control system 36 then retracts the measuring chamber bottom plate 302 to the 'Opened' position, thereby depositing the object sample into the target data acquisition cup 172. Subsequently, the control system 36 moves the target data acquisition cup 172 and object sample deposited therein to a location beneath the data collection instrument 256. More specifically, the target data acquisition cup 172 and respective object sample are moved to a position within a measurement field of the data collection instrument 256, via operation of the X-Y stage 262. Once the respective object sample is presented within the measurement field of the data collection instrument 256, the data collection instrument 256 analyzes the object sample, as described below. In various embodiments, via control of the X-Y stage 262, the respective control system 36 can move the target data acquisition cup 172 and respective object sample in a particular pattern within the measurement field of the data collection instrument 256, e.g., a circular pattern.

In various embodiments, each data acquisition cup 172 corresponds to a range of object sample volumes to be deposited into each respective data acquisition cup 172. The object sample volume ranges for the plurality of data acquisition cups 172 can overlap so that a wide range of volumes of object samples can be analyzed by each workstation 22. In various embodiments, the respective control system 36 selects the target data acquisition cup 172 such that when the object sample is deposited into the selected target data acquisition cup 172 the object sample will fill the target data acquisition cup 172 to a desired depth predetermined to provide accurate analysis.

Figure 12:
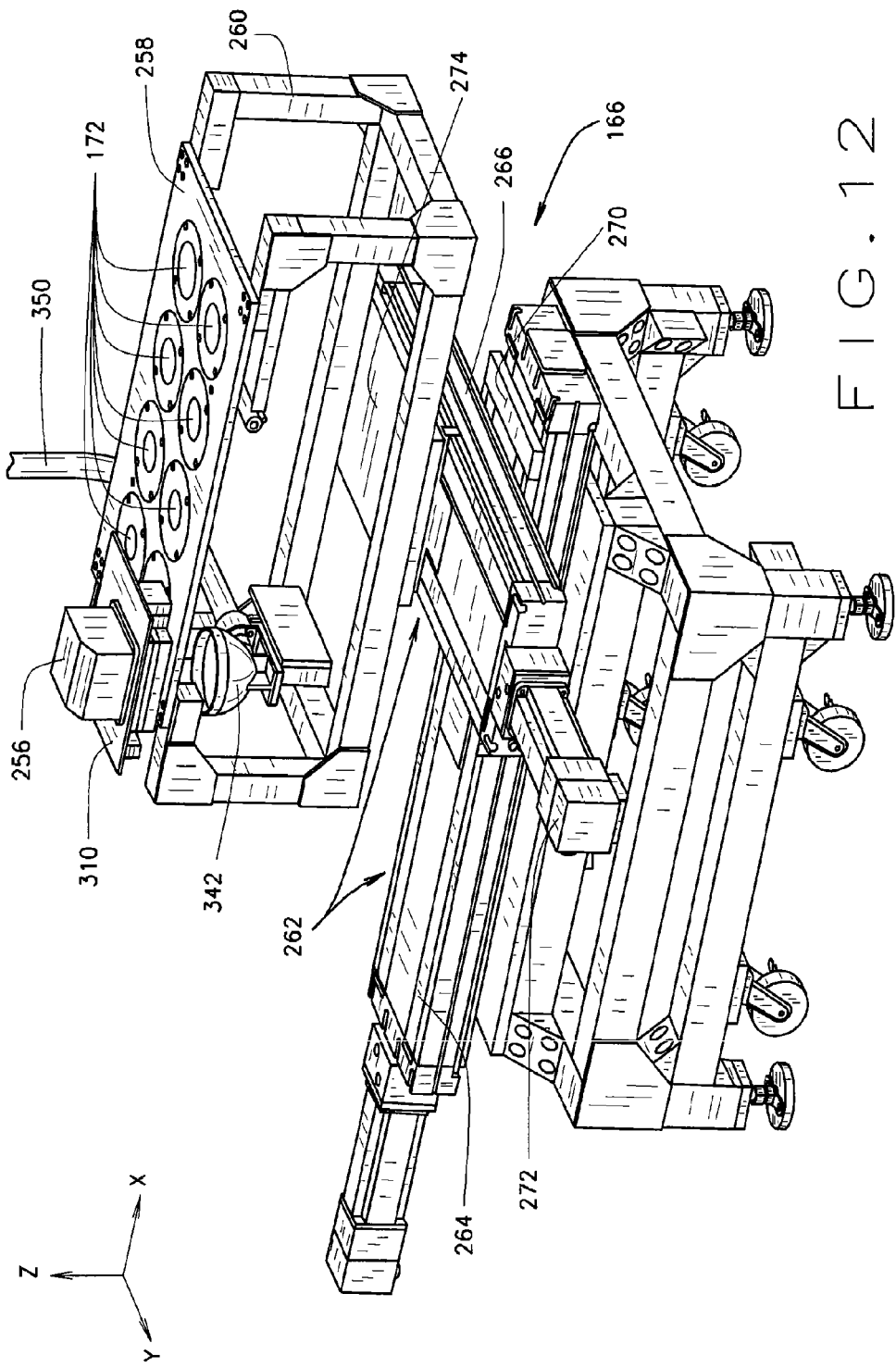
FIG. 12 is an isometric view of a data collection assembly of the automated analysis subsystem shown in FIG. 4, in accordance with various embodiments of the present disclosure.

Referring now to FIGS. 4 and 12, each data collection instrument 256 is communicatively connected to the respective control system 36 to analyze each respective object sample presented within the measurement field. Each respective data collection instrument 256 can be any type of data collection instrument operable to collect any desired type of data. For example, in various embodiments, each respective data collection instrument 256 can be operable to acquire data using visual image data (e.g., digital image data), or near infra-red (NIR) image data, or nuclear magnetic resonance (NMR) image data, or magnetic resonance imaging (MRI) data, or X-ray imaging data, or computed tomography (CT) image data, or any other type image data. Still further, in various embodiments, each data collection instrument 256 of the small object analysis system 10 can be the same type of data collection instrument operable to acquire the same type of data. Alternatively, in various embodiments, each data collection instrument 256 can be the same type of collection device, wherein one or more data collection instruments 256 of the small object analysis system 10 is configured to acquire different data than at least one other data collection instrument 256. Further yet, in various other embodiments, one or more of the data collection instruments 256 can be a different type of data collection instrument than at least one other data collection instrument 256 of the small object analysis system 10, wherein the one or more different data collection instrument(s) 256 is/are configured to acquire different data than at least one other data collection instrument 256.

Figure 15:
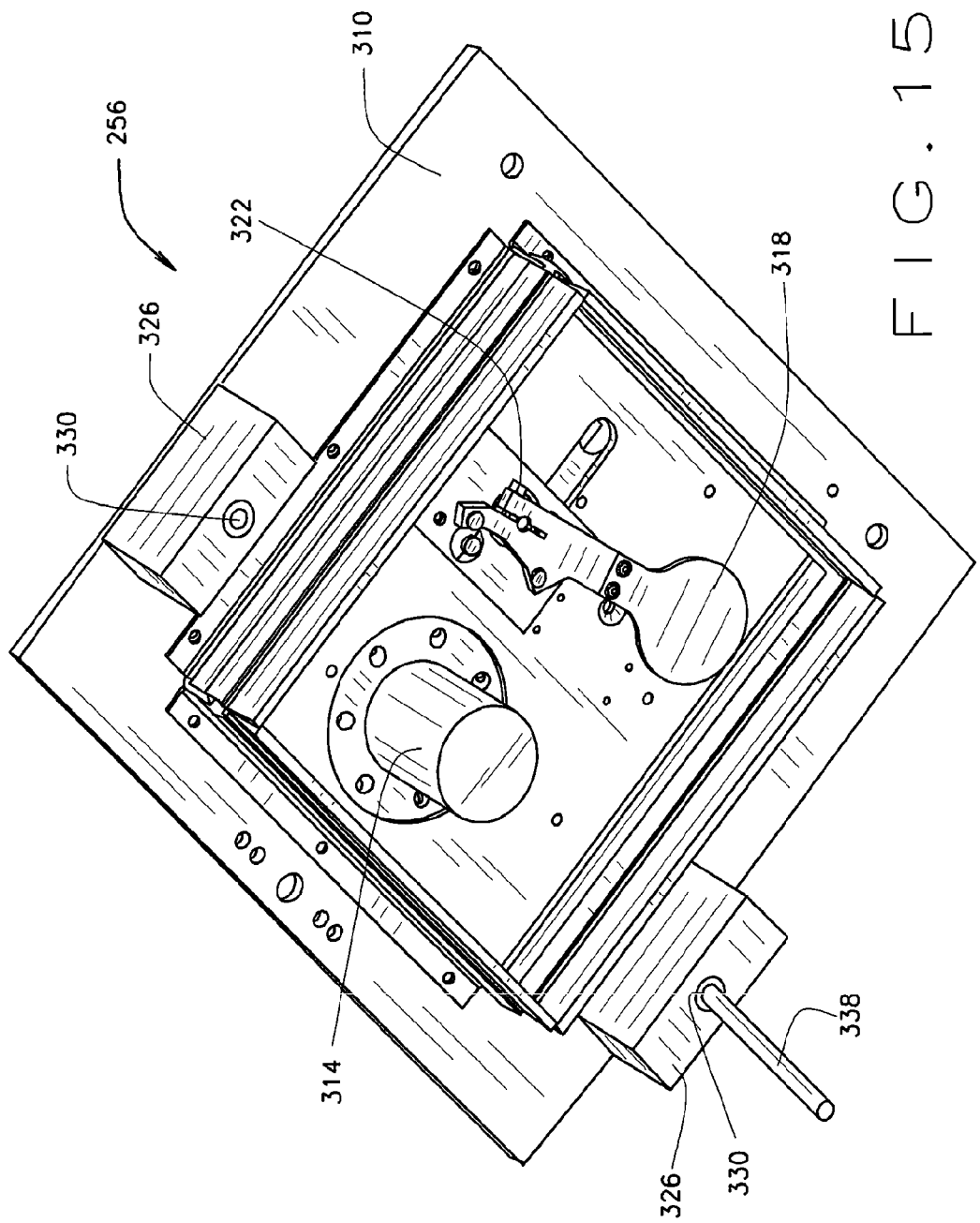
FIG. 15 is an isometric bottom view of a data collection instrument, in accordance with various embodiments of the present disclosure.

For example, with reference to FIGS. 4, 12 and 15, in various embodiments, at least one of the workstations 22 can include a NIR data collection instrument 256 operable to acquire NIR image data that is stored and interpreted by the respective control system 36 to identify one or more traits of each respective object sample. In such embodiments, the NIR data collection instrument 256 can be mounted to a mounting plate 310 that is connected to system support structure such that each respective NIR data collection instrument 256 remains at a constant location within the respective analysis subsystem 34. Once the target data acquisition cup 172 and respective object sample are positioned beneath the NIR data collection instrument 256, i.e., within the respective measurement field, the NIR data collection instrument 256 emits an NIR beam 314 and communicates the acquired NIR data to the respective control system 36. The control system 36 interprets, e.g., analyzes, the acquired NIR data to identify one or more traits of the respective object sample, and maps the data to one or more electronic databases, spreadsheets and/or look-up tables of the respective control system 36, as described above. More particularly, the control system 36 maps the data to one or more electronic databases, spreadsheets and/or look-up tables that link the data to the respective sample container 14 from which the object sample was dispensed by the respective container processing assembly 42.

In various embodiments, to interpret the acquired NIR data, the respective control system 36 utilizes empirical data indicative of NIR responses to the various known traits of the type of small objects to be analyzed by each respective workstation 22 of the small object analysis system 10. For example, empirical NIR data acquired from object samples with known traits, e.g., seed having known percents of proteins, starch, water, oil, sugar, etc., can be stored in electronic memory of each respective control system 36. Subsequently, as each object sample is NIR scanned by the respective NIR data collection instrument 256, the wavelength, frequencies and/or band of frequencies of the NIR response of the scanned object sample is compared to the known responses and evaluated. The evaluation can determine whether each respective object sample possesses various particular traits. For example, the object samples can comprise a particular seed type, e.g., corn seed, and evaluation of the acquired NIR data can determine a percentage of various constituents, such as proteins, starch, water, oil, sugar, etc., within each seed sample. That is, the stored empirical data provides a particular known response for each constituent and the NIR response of the scanned sample is compared to these known responses to determine a percent of each constituent within the sample. This data is then mapped to the particular corresponding sample container 14 in the one or more electronic databases, spreadsheets and/or look-up tables, utilizing the unique identification information collected using the identification device 150, as described above.

Additionally, in various embodiments, the NIR beam 314 can be an annular beam having an annular measurement field. In such embodiments, the control system 36 can move the target data acquisition cup 172 and respective object sample in a particular pattern within the annular measurement field to acquire more comprehensive data of the respective object sample. For example, via operation of the X-Y translation stage 262, each respective object sample can be moved in a circular pattern within the annular NIR annular measurement field such that the entire object sample is 'scanned'. Thus, a more comprehensive set of data can be acquired and analyzed to more accurately identify the one or more traits exhibited in each respective object sample.

As described above, in various embodiments, the respective control system 36 selects the target data acquisition cup 172 such that when the object sample is deposited into the selected target data acquisition cup 172 the object sample will fill the target data acquisition cup 172 to a desired depth predetermined to provide accurate data collection. For example, in the various embodiments wherein each data collection instruments 256 is a NIR data collection instrument, a predetermined depth of objects deposited into the target sample cup 172 can be desired. Providing a particular depth of each object sample within each respective target sample cup 172 will insure that the NIR beam 314 does not penetrate the depth of the object sample and acquire skewed data that would include data, i.e., noise, relating to the bottom of the sample cup 172.

Referring particularly to FIG. 15, in the embodiments wherein the data collection instrument 256 comprises an NIR data collection instrument, the NIR data collection instrument 256 can include a calibration, or tuning, flag 318 for establishing a baseline prior to scanning of each object sample. Establishing a baseline prior to the NIR scanning of each respective object sample will correct, or compensate, for adverse temperature affects on the NIR data collection instrument 256. The calibration flag 318 can be a ceramic flag coupled to an actuator 322, e.g., a motor, solenoid, or other device, operable to move the calibration flag 318 between a stowed position and a calibration position. More particularly, prior to the NIR scanning of each respective object sample, the calibration flag 318 is moved to the calibration position, wherein the calibration flag 318 is positioned under the annular NIR beam 314. The NIR data collection instrument 256 can then project the NIR beam 314 onto the calibration flag 318 and self-calibrate based on the returned NIR beam sensed by the NIR data collection instrument 256. Once the NIR data collection instrument 256 is calibrated, the calibration flag 318 is moved to the stowed position (as illustrated in FIG. 15), wherein respective object sample can be scanned by the NIR data collection instrument 256 to acquire the respective data, as described above.

Figure 13:
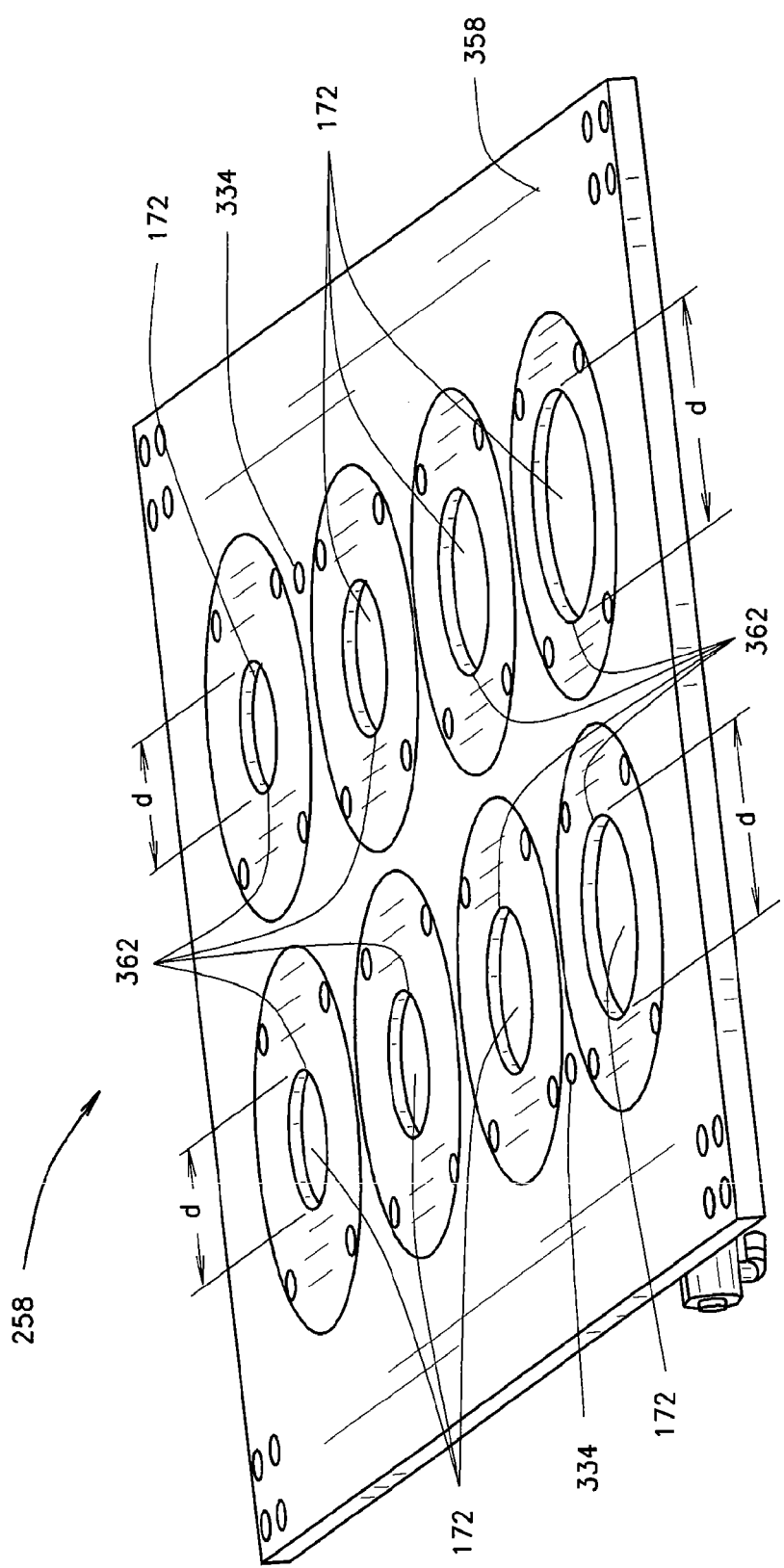
FIG. 13 is an isometric view of a presentation tray included in the data collection assembly shown in FIG. 12, in accordance with various embodiments of the present disclosure.
Figure 14:
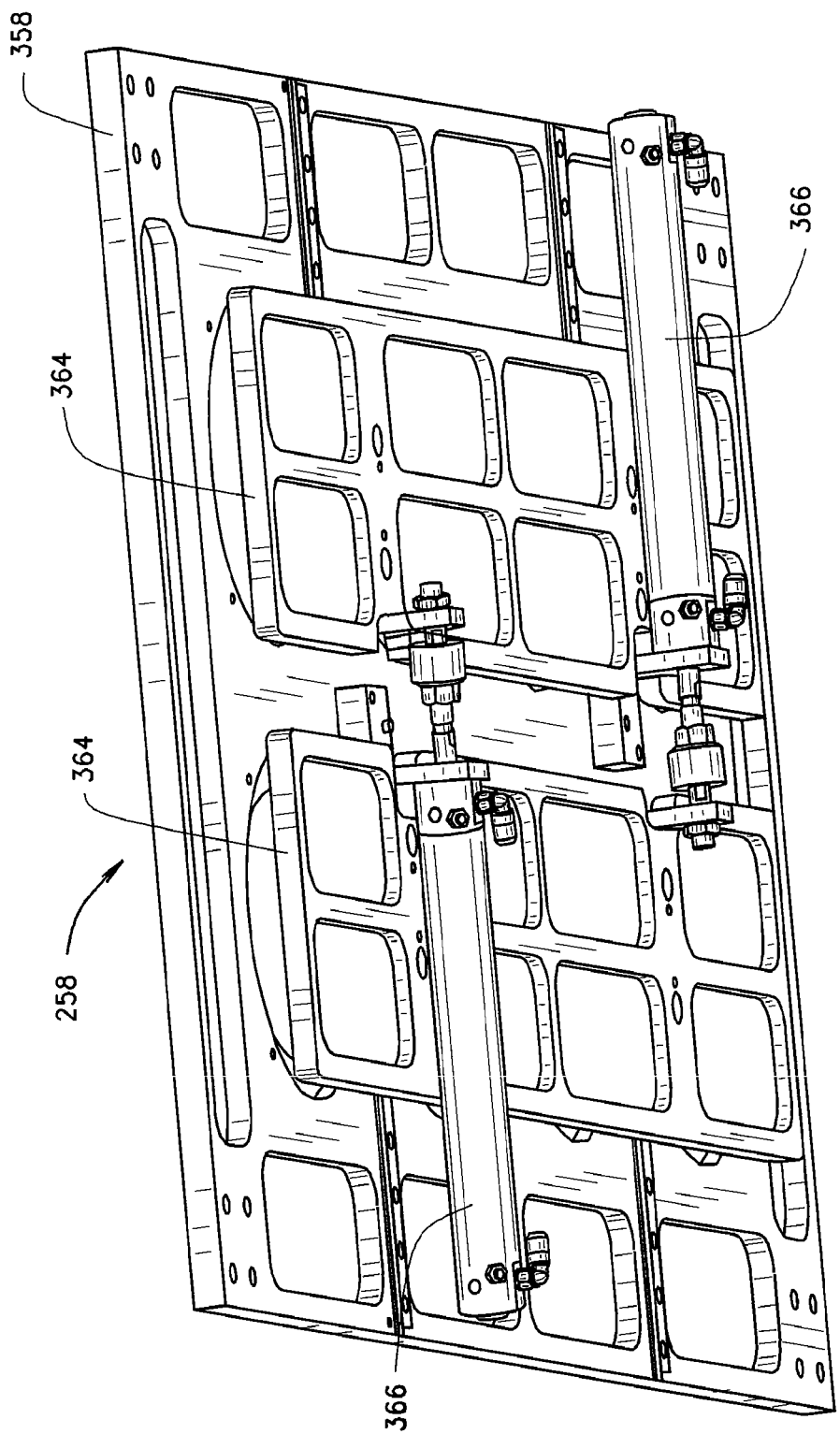
FIG. 14 is an isometric bottom view of the presentation tray shown in FIG. 13, in accordance with various embodiments of the present disclosure.

Referring now to FIGS. 13 and 15, in various embodiments, each data collection assembly 166 includes at least two teaching fixtures 326 that are structured and operable to recalibrate the location of each presentation tray 258 within the respective analysis subsystem 34. More specifically, the teaching fixtures are adapted to calibrate each data acquisition cup 172 within the X-Y coordinate system of the presentation tray 258 with respect to each of the respective height measurement modules measuring chambers 242 and the respective data collection instrument 256. For example, in various embodiments, each data collection assembly 166 includes a pair manual teaching fixtures 326 mounted to the data collection instrument mounting plate 310. More particularly, each manual teaching fixture 326 can comprise a block having a calibration bore 330 extending through each teaching fixture 326 and the mounting plate 310. Additionally, each respective presentation tray 258 can include a pair of calibration holes 334. Therefore, to recalibrate the location of each presentation tray 258 within the respective analysis subsystem 34, prior to operation of the respective workstation 22, a calibration rod 338 can be inserted though each calibration bore 330 (for simplicity, only one calibration rod is illustrated in FIG. 15). The respective presentation tray 258 is then moved to a position wherein each of the calibration rods 338 can be also inserted into a corresponding one of the respective calibration holes 334 in the presentation tray 258. The respective control system 36 can then denote, as a starting location, the position of the presentation tray 258, wherein the calibration rods 338 align the calibration bores 330 of the teaching fixtures 326 with the calibration holes 334 of the presentation tray 258. Moreover, utilizing the denoted starting position of the presentation tray 258, the control system 36 can calculate the location of each respective data acquisition cup 172 within the presentation tray 258. Thus, during operation, each respective target data acquisition cup 172 can be accurately positioned beneath the respective height measurement modules measuring chambers 242 to receive each object sample, and beneath the respective data collection instrument 256 to collecting the data, as described above.

Referring now to FIGS. 12, 13, 14 and 16, as set forth above, in various embodiments, each analysis subsystem 34 includes the object return assembly 170. Each object return assembly 170 is structured and operable to collect each object sample from the respective data acquisition cup 172, subsequent to the acquisition and mapping of the respective data, and return each object sample to the respective original sample container 14. In various embodiments, each object return assembly 170 includes a sample transfer funnel 342 stationarily mounted to system support structure, a deceleration and diverter subassembly 346 fluidly connected to the sample transfer funnel 342 via an object transfer tube 350, and a plurality of sample return tubes 354 connected to the deceleration and diverter subassembly 346. Generally, after each object sample is analyzed, via the respective data collection instrument 356, each object sample is deposited into the sample transfer funnel 342 where each object sample is transferred through the transfer tube 350, via vacuum and/or forced air. Each object sample is then selectively diverted, via the deceleration and diverter subassembly 346, to one of the sample return tubes 354 that channel each object sample into the sample container 14 from which each respective object sample was originally dispensed.

Additionally, in various embodiments, each presentation tray 258 comprises a top panel 358 that includes a plurality of cup apertures 362 and at least one bottom panel 364 slideably mounted to the top panel 358 to move between a 'Closed' position and an 'Opened' position. In such embodiments, each presentation tray 258 additionally includes an actuator 366 connected to each bottom panel 364 and operable to, as controlled by the respective control system 36, move the respective bottom panel 364 between the 'Closed' and the 'Opened' positions. In the 'Closed' position, the bottom panel (s) 364 cover(s) each of the cup apertures 362 to form the data acquisition cups 172. Moreover, each cup aperture 362 has a different diameter d such that each data acquisition cup 172 of each respective presentation tray 258 has different interior volume, as described above. In the 'Opened' position the bottom panel(s) 364 are moved away from the cup apertures 362 such that each analyzed object sample is evacuated from the respective data acquisition cup 172, via gravity, vacuum and/or forced air, and deposited into the sample transfer funnel 342.

Thus, after the data is acquired and mapped for each respective object sample, the respective control system 36 moves the presentation tray 258, via operation of the X-Y translation stage 262, such that the target data acquisition cup 172 containing the analyzed object sample is positioned directly above the respective sample transfer funnel 342. Once the target data acquisition cup 172 is positioned above the collection funnel, the control system 36 activates the presentation tray bottom panel actuator(s) 366 to move the respective bottom panel(s) 364 to the 'Opened' positioned. Thereafter, the respective analyzed object sample is dispensed from the respective data acquisition cup 172 into the sample transfer funnel 342.

Figure 16:
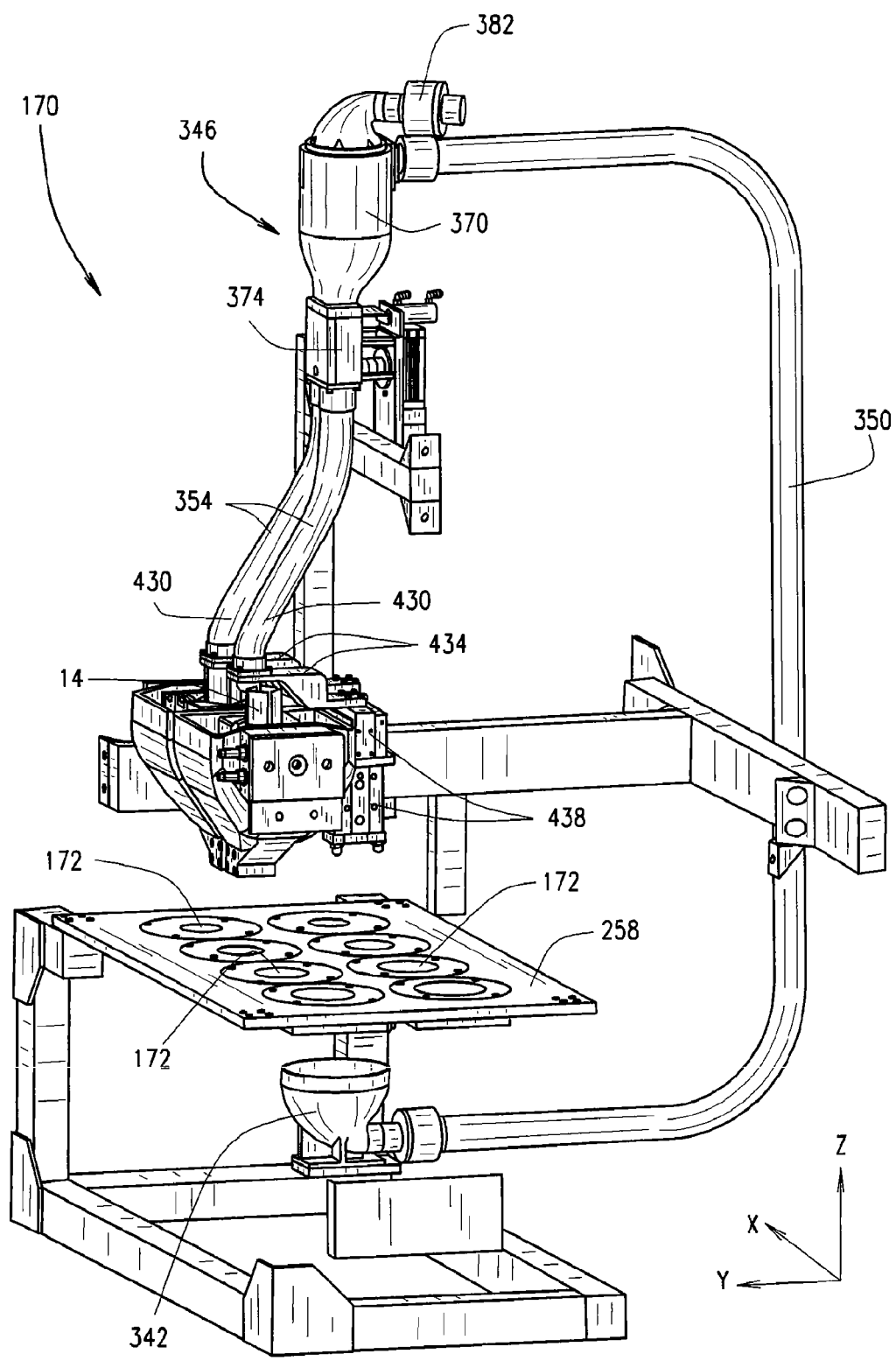
FIG. 16 is an isometric view of an object return assembly included in the automated analysis subsystem shown in FIG. 4, in accordance with various embodiments of the present disclosure.
Figure 17:
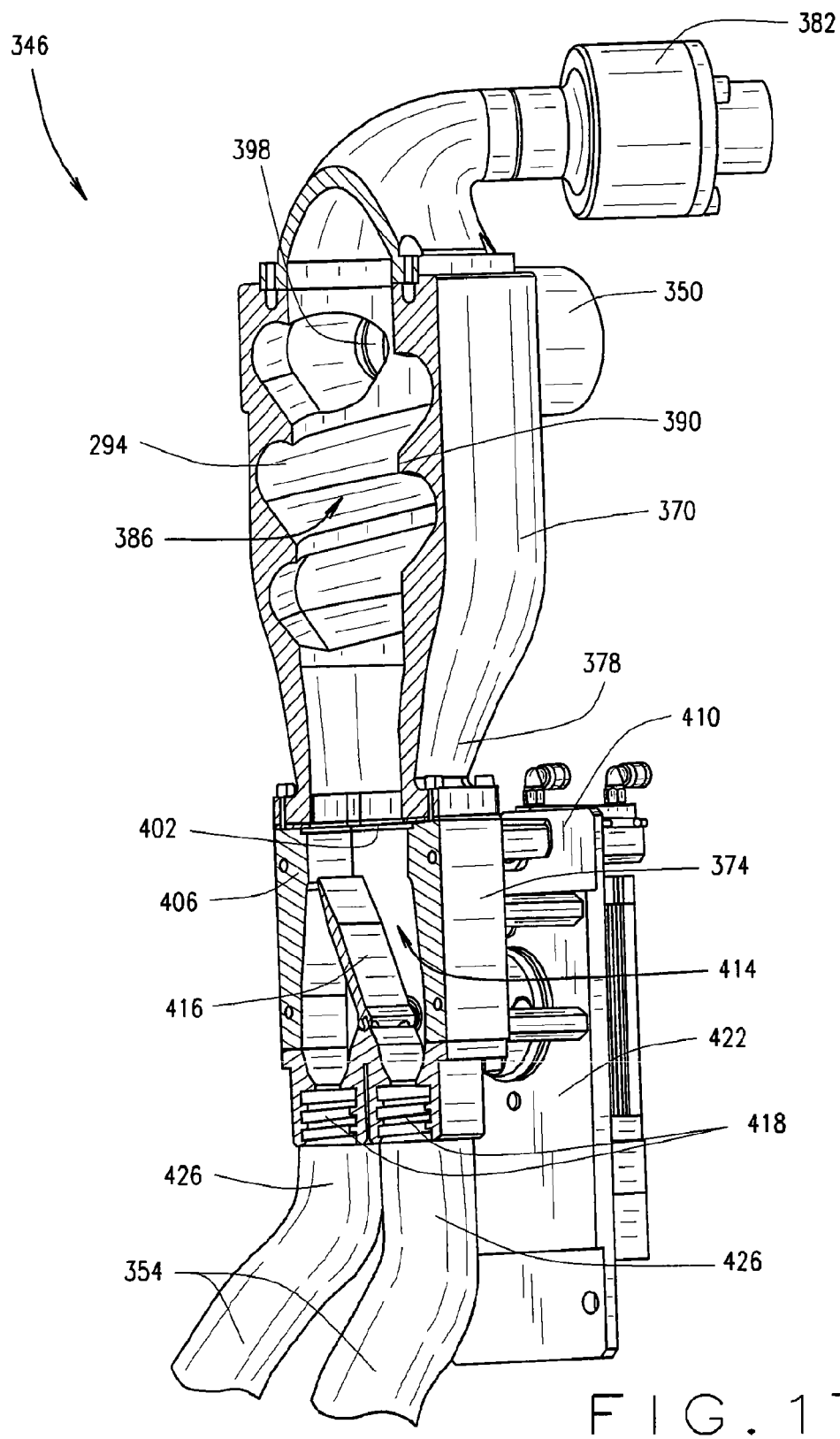
FIG. 17 is an isometric cross-sectional view of deceleration and diverter subassembly of the object return assembly shown in FIG. 16, in accordance with various embodiments of the present disclosure.

Referring now to FIGS. 16 and 17, in various embodiments, each deceleration and diverter subassembly 346 includes a deceleration chamber 370 and a diverter chamber 374 coupled to a disposition end 378 the deceleration chamber 370. Additionally, the object return assembly 170 can further include a vacuum generator 382 that is operational, as controlled by the respective control system 36, to generate a vacuum within the respective transfer tube 350. The generated vacuum is of sufficient force to transfer, i.e., propel, each object sample dispensed into the respective sample transfer funnel 342 from the sample transfer funnel 342, through the transfer tube 350, and into the respective deceleration chamber 370.

In various embodiments, each deceleration chamber 370 includes an interior compartment 386 that includes an outer wall 390 having a spiral channel 394 formed therein. Moreover, each deceleration chamber includes an inlet port 398 connected to the respective transfer tube 350 and directing each transferred object sample into the respective spiral channel 394. Thus, each object sample transferred from the sample transfer funnel 342 will enter the respective deceleration chamber interior compartment 386, via the inlet port 398, and travel in circular motion along the respective interior compartment outer wall 390, within the respective spiral channel 394. As each respective object sample travels within the spiral channel 394 the kinetic energy of the object sample will be absorbed and the transfer speed, with which the object sample entered the respective deceleration chamber interior compartment 386, will be decreased.

In various implementations, the deceleration and diverter subassembly 346 further includes an accumulator sluice plate 402 slideable mounted between the disposition end 378 of the deceleration chamber 370 and an intake end 406 of the diverter chamber 374. Each accumulator sluice plate 402 is connected to a respective linear actuator 410 that is operable, as controlled by the respective control system 36, to selectively move the accumulator sluice plate 402 between a 'Closed' position and an 'Opened' position. When the accumulator sluice plate 402 is placed in the 'Closed' position, a decelerated object sample will be blocked from entering the respective diverter chamber 374 and be accumulated within the respective deceleration chamber interior compartment 386, at the disposition end 378 of the deceleration chamber 370. When the accumulator sluice plate 402 is placed in the 'Opened' position, a decelerated object sample will be allowed to enter the respective diverter chamber 374.

More particularly, in various embodiments, each diverter chamber 374 includes an interior compartment 414, a diverter gate 416 pivotally mounted within the interior compartment 414 and plurality of exit ports 418. As illustrated in FIG. 17, the diverter chamber 374 is coupled to the deceleration chamber 370 such that each respective object sample will pass from the deceleration chamber interior compartment 386 into the diverter chamber interior compartment 414. Additionally, each exit port 418 is connected to a corresponding one of the sample return tubes 354 and the diverter gate 416 is coupled to a rotary actuator 422 operable, as controlled by the respective control system 36, to selectively position the diverter gate 416 in one of a plurality of diverting positions. Each diverting position will direct a respective object sample that enters the diverter chamber interior compartment 414 to a selected one of the return tubes 354, as described further below.

Referring now to FIGS. 11 and 16, each sample return tube 354 is connected to a corresponding one of the diverter chamber exit ports 418, as described above, at an inlet end 426. An outlet end 430 of each sample return tube terminates at, and is connected to, a respective guide plate 434. Each guide plate 434 is connected to a pair of linear actuators 438 that are operable, as controlled by the respective control system 36, to selectively move the outlet end 430 of the respective return tube 354 within a Z-Y plane of the object return assembly 170. More specifically, to return an object sample to the original sample container 14 from which the respective returning object sample was originally dispensed, the linear actuators 438 are moved within the Z-Y plane to position the outlet end 430 of the respective return tube 354 above the original sample container 14 that is still retained within the corresponding object dispensing module 174.

Still more specifically, during the processing and analyzing of each object sample, as described above, the respective control system 36 keeps track of which object dispensing module 174 retains the corresponding original sample container 14 from which the respective object sample was originally dispensed. Additionally, prior to, during or after transferring each respective analyzed object sample from the sample transfer funnel 342 to the deceleration chamber 370, the respective control system 36 will position the outlet end 430 of one of the return tubes 354 above the original sample container 14. Furthermore, prior to, during or after transferring each respective analyzed object sample from the sample transfer funnel 342, the respective control system 36 will command the diverter gate rotary actuator 422 to move the diverter gate 416 to a position that will direct the respective object sample to the sample return tube 354 that has the corresponding outlet end 430 positioned above the original sample container 14.

Accordingly, when a respective object sample is returned, i.e., transferred from the sample transfer funnel 342 to the deceleration chamber 370, the object sample will travel through the deceleration chamber 370, where the speed of the object sample will be reduced as described above, and into the diverter chamber 374. Then, via the diverter gate 416, the respective object sample will be directed toward the sample return tube 354 that has the corresponding outlet end 430 positioned above the original sample container 14. The respective object sample will then travel through the respective sample return tube 354, via gravity, vacuum and/or forced air, and be deposited into the corresponding original sample container 14 from which the object sample was originally dispensed. Accordingly, the respective analyzed object sample will be returned from the transfer funnel 342 and redeposited into the original sample container 14 from which the respective object sample was originally dispensed.

In various embodiments, prior to an object sample being transferred from the sample transfer funnel 342 to the deceleration chamber 370, the respective control system 36 will move the accumulator sluice plate 402 to the 'Closed' position. Accordingly, as the respective object sample travels through the deceleration chamber 370, the sample will be blocked from traveling into the diverter chamber 374 and accumulate on accumulator sluice plate 402. Subsequently, the control system 36 will move the accumulator sluice plate 402 to the 'Opened' position such that the accumulated object sample is dispensed into the diverter chamber where the object sample is diverted, via the diverter gate 416, into the appropriate sample return tube 354. Accordingly, the respective analyzed object sample will be returned from the transfer funnel 342 and redeposited into the original sample container 14 from which the respective object sample was originally dispensed.

As described above, in various embodiments, each analysis subsystem 34 further includes at least one container cap handling assembly 218 for each container processing assembly 42. In such embodiments, subsequent to each object sample being redeposited into the original sample container 14, the respective control system 36 moves the respective cap grasping device 222 from the 'Retracted' position to the 'Extended' position. Thus, the respective cap clasping claw 234, having the respective sample container cap 214 grasped therein, will be located directly above the sample container 14. The control system 36 then operates the cap handling assembly first actuator 226 to lower the respective cap grasping device 222 such that the respective cap clasping claw 234 replaces the cap 214 onto the respective sample container 14. Subsequently, the control system 36 opens the cap clasping claw 234 to release the cap 214 and returns cap grasping device 222 to the 'Retracted' position.

The respective control system 36 then operates the sample container handling robot 38 to retrieve each refilled and recapped sample container 14 from the respective sample container processing assembly and place the retrieved sample container 14 back into the well 102 of the original sample tray 12 from which the respective sample container 14 was originally removed. After all the object samples within a particular sample tray 12 have been analyzed, as described above, the tray shuttle robot 26 removes the sample tray 12 from the respective workstation 22, replaces the removed sample tray 12 with a subsequent sample tray 12 populated with object samples to be analyzed, and returns the removed tray 12 to the tray staging console 18.

Figure 18:
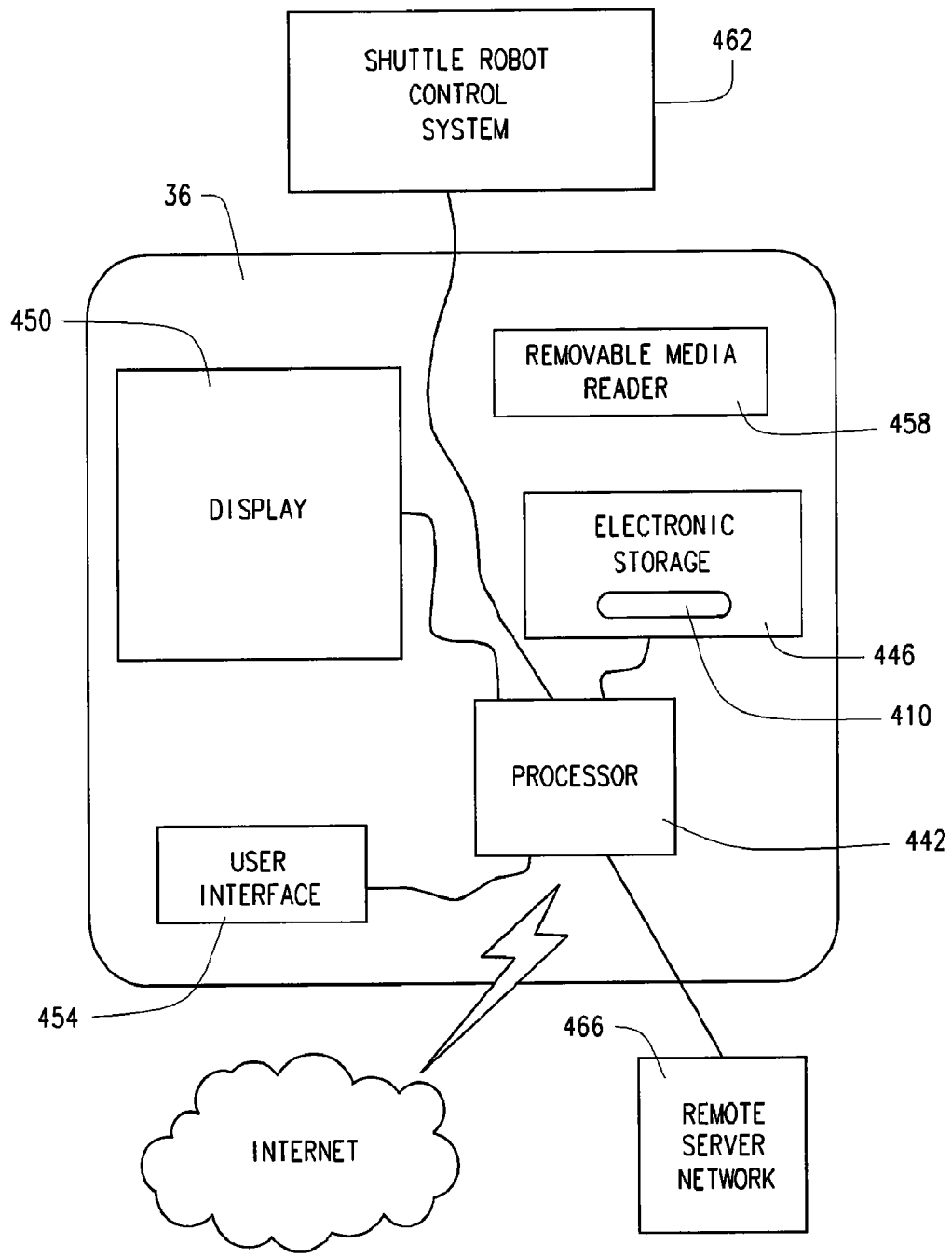
FIG. 18 is a block diagram of a control system for each workstation shown of the small object analysis system shown in FIG. 1, in accordance with various embodiments of the present disclosure.

Referring to FIG. 18, in various embodiments, the respective control system 36 of each workstation 22 can be a computer based system that generally includes at least one processor 442 suitable to execute all functions of the respective control system 36 to automatically, or robotically, control the operation of the respective workstation 22, as described herein. Each control system 36 can additionally include at least one electronic storage device 446 that comprises a computer readable medium, such as a hard drive or any other electronic data storage device for storing such things as software packages or programs, algorithms and digital information, data, look-up tables, electronic spreadsheets and databases. Furthermore, each control system 36 can include a display 450 for displaying such things as information, data and/or graphical representations, and at least one user interface device 454, such as a keyboard, mouse, stylus, scanner and/or an interactive touch-screen on the display 450. In various embodiments each control system 36 can further include a removable media reader 458 for reading information and data from, and/or writing information and data to, removable electronic storage media such as floppy disks, compact disks, DVD disks, zip disks, or any other computer readable removable and portable electronic storage media. In various embodiments, the removable media reader 458 can be an I/O port of the respective control system 36 utilized to read external or peripheral memory devices such as thumb drives, memory sticks/cards or external hard drives.

In various embodiments, each control system 36 is communicatively connectable to a shuttle robot control system 462 to coordinate the operation of the tray shuttle robot 26 with the operations of each respective workstation 22, i.e., the shuttling of sample trays 12 to and from each of the workstations 22. Similar to each workstation control system 36, the shuttle robot control system 462 can include at least one processor (not shown), at least one electronic storage device (not shown), a display (not shown), at least one user interface device (not shown) and removable media reader (not shown) utilized to perform the operations of the shuttle robot control system 462.

Additionally, in various embodiments, each workstation control system 36 can be communicatively connectable to a server network 466, e.g., a local area network (LAN), via a wired or wireless link. Accordingly, each control system 36 can communicate with the remote server network 466 to upload and/or download data, information, algorithms, software programs, etc., and/or receive operational commands. Additionally, in various embodiments, each control system 36 can be configured to access the Internet to upload and/or download data, information, algorithms, software programs, etc., to and from Internet sites and network servers.

Additionally, in various embodiments, each control system 36 includes a small object analysis program 470, stored on the storage device 446 and executed by processor 442 using inputs from the user interface 454 and various components, sensors, systems and assemblies of the respective workstation 22. Particularly, the small object analysis program 470 can include various custom programs, applications, routines, subroutines and/or algorithms that are executable by the processor 442 to effectuate and control the operation of each respective workstation 22.

Although each workstation control system 36 is generally illustrated as a single computer based system, each workstation control system 36 can comprise a plurality of computer based subsystems networked together to coordinate the simultaneous operations of the respective workstation. For example, in various embodiments, each control system 36 can include a main controller subsystem networked together with a plurality of peripheral controller subsystems (not shown), e.g., a peripheral controller subsystem for each of the container transfer subsystem 30 and the analysis subsystem 34.

Each peripheral controller subsystem can include one or more processors, microprocessors and electronic data storage devices that effectuate communication with respective subsystem components, e.g., sensors, devices, mechanisms, motors, tools, etc., and together with the main controller subsystem cooperatively operate all the systems, subsystems, assemblies, and subassemblies of the respective workstation 22.

As described above, each control system 36 communicates with various components and sensors of the respective workstation 22 to detect conditions of interest during operation of the respective workstation 22. With this information, each respective control system 36 can generate control commands that effectuate the operations and actions taken by the various systems, subsystems, assemblies, and subassemblies of the respective workstation 22. For example, a sensed condition can concern: the successful placement of an object sample container 14 into a respective container processing assembly 42; the successful deposit of an object sample into a respective volume measuring chamber 242; the proper disposition of an object sample into a target data acquisition cup 172; the completion of data acquisition for each respective object sample; the successful return of each analyzed object sample to the respective sample container 14; and the like. More specifically, information that is collected and processed for use in controlling operation of respective workstation 22 can include such information as: device or component status; error signals; movement; stall; position; location; temperature; voltage; current; pressure; and the like, which can be monitored with respect to the operation of each of the system, subsystems, assemblies, subassemblies and associated components of the respective workstation 22.

It should be understood that each workstation 22 is substantially identical in form and function. Thus, although the description herein of the small object analysis system 10 may at times refer to a single workstation 22 or a single particular component, assembly, subassembly, system and/or subsystem of a single workstation 22, it should be understood that such description is for simplicity and clarity, and is applicable each workstation 22 of the small object analysis system 10.

It should also be understood that each workstation 22 can be structured and operable to provide parallel processing and analysis of the sample containers 14 and respective objects samples of the sample trays 12 placed on the respective docking plate 90. That is, in various embodiments, each workstation 22 can remove a second sample container 14 from a respective sample tray 12 while the object sample of a previously removed sample container 14 is being analyzed, as described herein. Then, as the first object sample is being returned to respective sample container 14, via the object return assembly 170, the second object sample can be deposited into a respective target data acquisition cup 172 for analysis.

Figure 19:
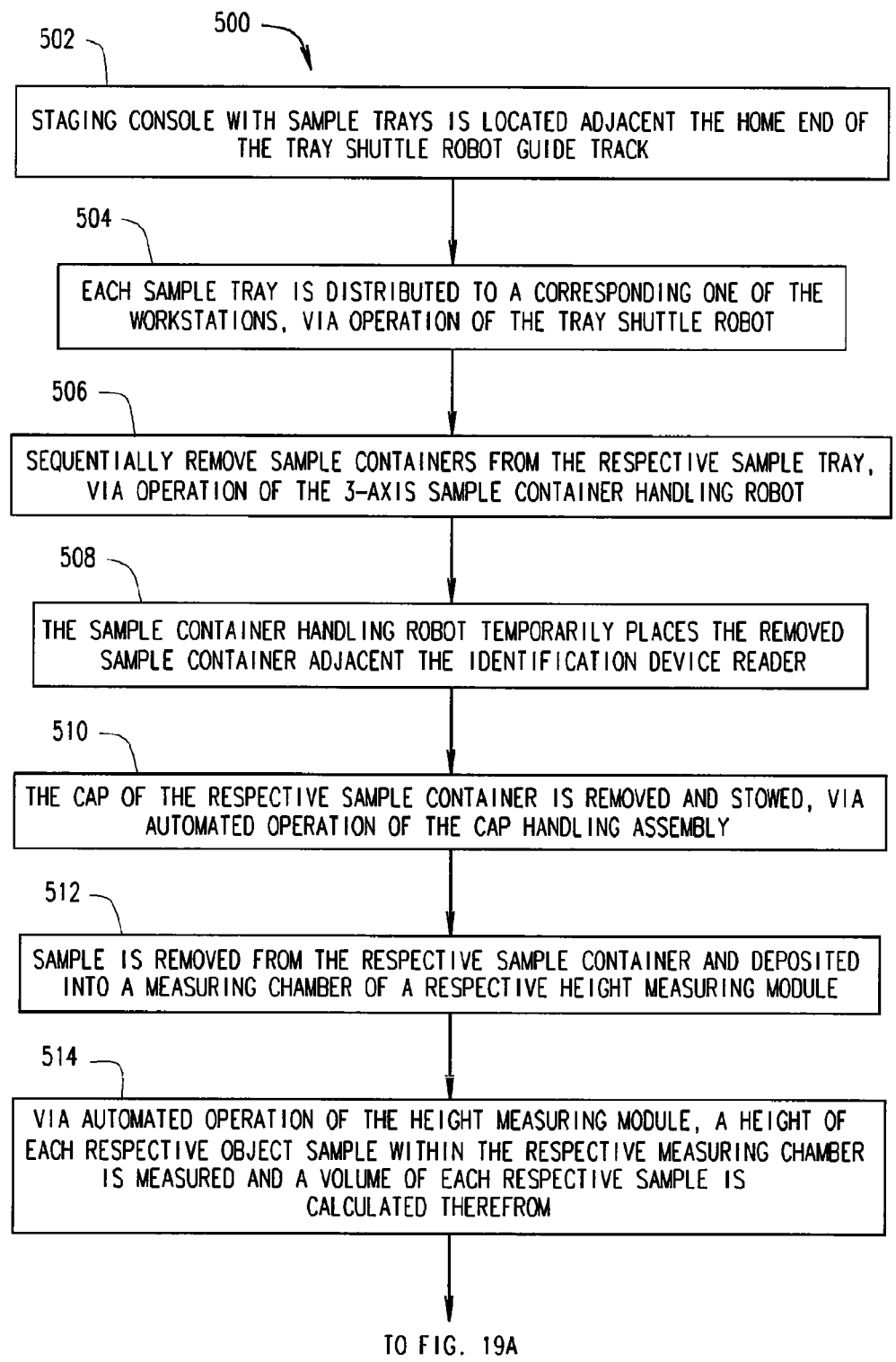
FIGS. 19 and 19A show a flow chart illustrating the operation of the small object analysis system shown throughout FIGS. 1 through 18, in accordance with various embodiments of the present disclosure.
Figure 19A:
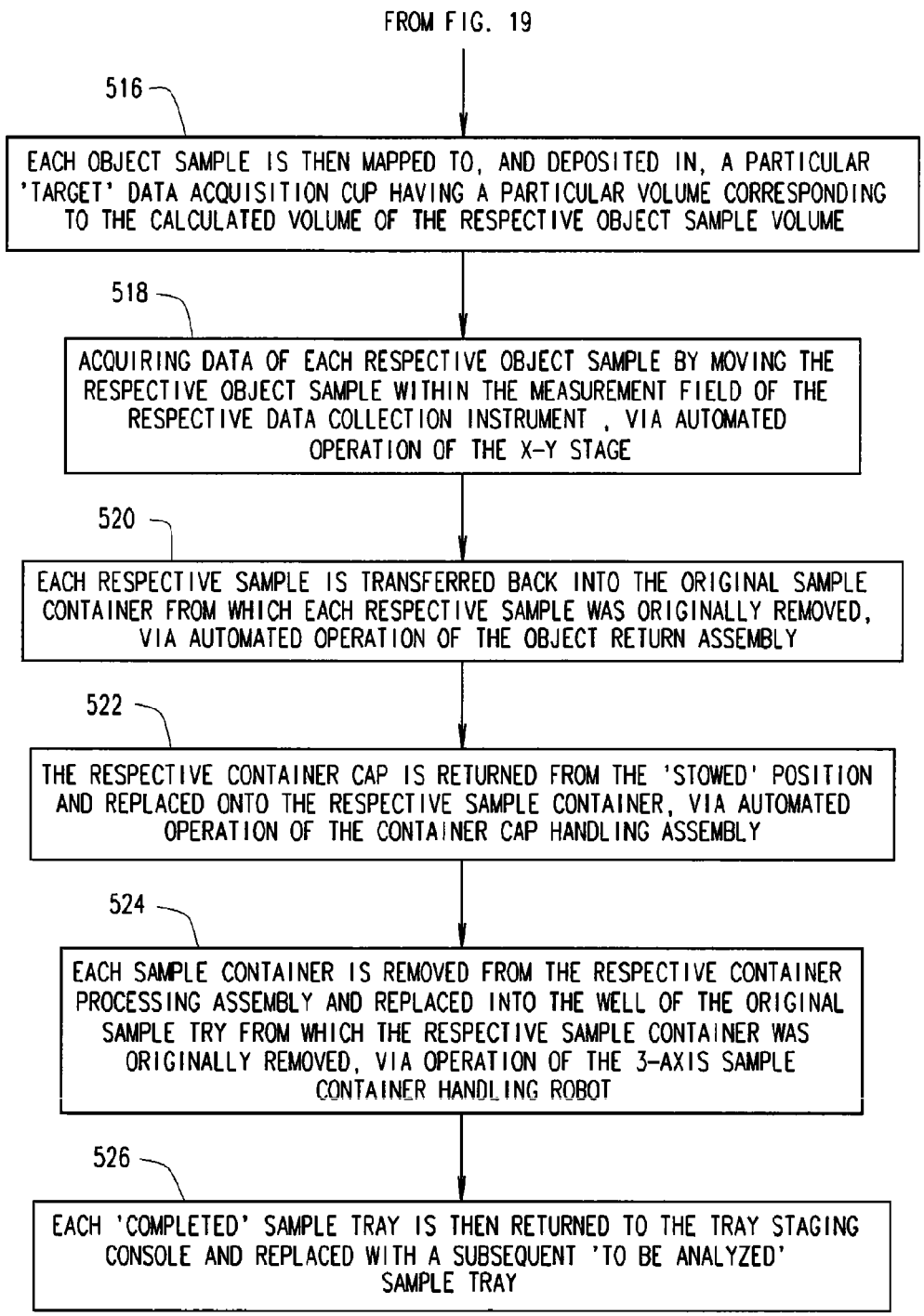

FIG. 19 provides a flow chart 500 illustrating the general operation of the small object analysis system 10, in accordance with various embodiments. Initially, a plurality of sample trays 12, populated with a plurality of arrayed sample containers 14, are supported on the staging console 18 at the tray staging location adjacent the home end 27 of the tray shuttle robot guide track 28, as illustrated at 502. Via the automated operation of the tray shuttle robot 26 along the guide track 28, each sample tray 12 is then distributed to a corresponding one of the workstations 22 located adjacent at least one side of the guide track 28, as illustrated at 504. Once a sample tray 12 has been distributed to a workstation 22, each sample container 14 is sequentially removed from the respective sample tray 12 and placed in one of the container processing assemblies 42, via operation of the 3-axis sample container handling robot 38, as indicated at 506.

In various embodiments, prior to placing each sample container 14 into one of the container processing assemblies 42, the sample container handling robot 38 temporarily places the removed sample container 14 adjacent the identification device reader 146 to obtain the unique identification information, i.e., data, relating to the respective sample container 14 and/or information, i.e., data, regarding the small object sample disposed within the respective sample container 14, as indicated at 508. Additionally, in various embodiments, after each sample container 14 is placed into one of the container processing assemblies 42, the container cap 214 is removed and moved to a 'Stowed' position, via automated operation of the container cap handling assembly 218, as indicated at 510.

Each respective object sample is then removed from the respective sample container 14 and deposited into a measuring chamber 242 of a respective height measuring module 178, as indicated a 512. Via automated operation of the height measuring module 178, a height of each respective object sample within the respective measuring chamber 242 is measured and a volume of each respective object sample is calculated therefrom, as indicated a 512. Each object sample is then mapped to, and deposited into, a particular 'target' data acquisition cup 172 having a particular volume corresponding to the calculated volume of the respective object sample volume, as indicated at 514. Thereafter, the data of each respective object sample is acquired by moving the target data acquisition cup 172 and respective object sample within the measurement field of the respective data collection instrument 256, e.g., an NIR data collection instrument, via automated operation of the X-Y stage 262, as indicated at 518. After the each respective object sample is analyzed, each respective sample is transferred back into the original sample container 14 from which each respective sample was originally removed, via automated operation of the object return assembly 170, as indicated 520.

In various embodiments, after each sample is returned to its original sample container 14, the respective container cap 214 is returned from the 'Stowed' position and replaced onto the respective sample container 14, via automated operation of the container cap handling assembly 218, as indicated at 522.

Subsequently, the 3-axis sample container handling robot 38 is utilized to remove each sample container 14 from the respective container processing assembly 42 and replace each sample container 14 into the well 102 of the original sample tray 12 from which the respective sample container 14 was originally removed, as indicated at 524. Once each object sample of a particular sample tray 12 has been analyzed and returned to the respective sample tray 12, the tray shuttle robot 26 removes the 'Completed' sample tray 12 from the respective workstation 22, replaces it with a subsequent 'To Be Analyzed' sample tray 12 and returns the 'Completed' tray 12 to the tray staging console 18, as indicated at 526.

Thus, the automated small object analysis systems and methods described herein, allow for high throughput handling, preparation and analysis of a plurality of samples of small objects, such as seeds. The systems and methods use robotics to process trays of queued object sample containers and analyze the small objects retained within each sample container. Additionally, the robotically controlled shuttling, loading, unloading and analyzing of the queued object samples, as described herein, provides increased throughput capacity, reduced staffing requirements, increased productivity and flexibility for expansion/reduction of the system.

When introducing elements or features of embodiments herein, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It should be understood that, although the terms first, second, third, etc. have been used herein to describe various elements, components, sections, regions, etc. These elements, components, sections, regions, etc., should not be misconstrued to indicate priority or importance elements, components, sections, regions, etc. These terms have been used merely to distinguish one element, component, section, region, etc., from another element, component, section, region, etc.

Furthermore, spatially relative terms, such as "beneath", "below", "lower", "above", "upper" and the like, as used herein are for ease of description to describe one element or feature's relationship to another element(s) or feature(s) as illustrated in the figures. It will be understood that the spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A system for analyzing a plurality of small objects, said system comprising:
   a staging console structured to support a plurality of sample trays populated with a plurality of arrayed sample containers, each sample container containing a respective object sample comprising a plurality of objects;
   a plurality of workstations structured and operable to analyze each object sample provided by each sample tray, each workstation comprising:
   a robotic container transfer subsystem structured and operable to sequentially remove and replace each of the sample containers arrayed in at least one of the sample trays;
   an automated analysis subsystem comprising:
      a data collection assembly structured and operable to analyze each respective object sample; and
      at least one processing assembly structured and operable to receive selected sample containers removed from the respective sample tray and placed into the processing assembly by a 3-axis sample container handling robot of the robotic container transfer subsystem, dispense each object sample, obtain data to determine the volume of the object sample contained within each respective sample container, and deposit each measured object sample into one of a plurality of data acquisition cups of the data collection assembly based on the volume of the respective object sample; and a tray shuttle robot structured and operable to remove each sample tray from the staging console, distribute each sample tray to a corresponding one of the workstations, retrieve the sample trays from the workstations, and return each sample tray to the staging console.

2. The system of claim 1, wherein each robotic container transfer subsystem comprises:

a 3-axis sample container handling robot structured and operable to sequentially remove each sample container from each sample tray distributed to the respective workstation and sequentially place each sample container into a processing assembly of the analysis subsystem of the respective workstation; and a sample tray queuing platform structured to accurately locate and orient each sample tray at the respective workstation, when distributed by the tray shuttle robot, such that the location of each respective sample container is coordinated with the operation of the sample container handling robot.

3. The system of claim 2, wherein each sample tray queuing platform comprises a docking plate that includes a plurality of tray locating fixture first halves, and a bottom plate of each sample tray includes a plurality of tray locating fixture second halves that mate with the tray locating fixture first halves to accurately locate and orient each sample tray on the respective sample tray queuing platform when distributed by the tray shuttle robot.

4. The system of claim 2, wherein each sample tray queuing platform comprises a tray locking mechanism first half, and a bottom plate of each sample tray includes a tray locking mechanism second half, and wherein the locking mechanism first and second halves are controllably engageable to steadily retain each respective sample tray on a docking plate of the respective sample tray queuing platform when distributed by the tray shuttle robot.

5. The system of claim 2, wherein each robotic container transfer subsystem further comprises a sample identification device reader structured and operable to read a sample identification device associated with each sample container as the sample container handling robot moves each sample container from the respective sample tray to the processing assembly of the respective workstation.

6. The system of claim 1, wherein each sample tray comprises:

a plurality of wells, each well structured to removeably retain a respective one of the sample containers; and a bottom plate that includes a plurality of windows, each window aligning with a corresponding one of the wells such that a sample identification device on the bottom of each respective sample container can be viewed through the respective window.

7. The system of claim 1, wherein each processing assembly comprises:

a height measurement module structured and operable to obtain data to determine the volume of the object sample contained within each respective sample container; and an object dispensing module structured and operable to dispense the object sample from each respective sample container into the height measurement module.

8. The system of claim 7, wherein each object dispensing module comprises:

a dispensing funnel structured to funnel each object sample into the height measurement module; and a rotatable container retention block structured and operable to retain each sample container received from the sample container handling robot, and dispense each sample into the dispensing funnel.

9. The system of claim 8, wherein each height measurement module comprises:

a measuring chamber structured to receive each object sample dispensed from the dispensing module and having a predetermined cross-sectional area; and a height measurement device operable to measure the height of each object sample within the measuring chamber so that a volume of each object sample can be calculated using the cross-sectional area of the measuring chamber and the measured height of each respective object sample within the measuring chamber.

10. The system of claim 9, wherein each measuring chamber comprises a retractable bottom movable between a 'Closed' position for retaining each object sample within the measuring chamber and an 'Opened' position for depositing each respective measured object sample into one of the data acquisition cups of the data collection assembly.

11. The system of claim 1, wherein each data collection assembly comprises:

a data collection instrument structured and operable to acquire the data for each respective object sample deposited into the data acquisition cups; and a presentation tray including the plurality of data acquisition cups and mounted to an X-Y stage structured and operable to move each respective object sample within a measurement field of the data collection instrument.

12. The system of claim 11, wherein a depth of each data acquisition cup is substantially equal to the depth of each of the other data acquisition cups, and a diameter of each data acquisition cup is different than the diameter of each of the other data acquisition cups such that each data acquisition cup has a different interior volume to accommodate different volumes of the object samples.

13. The system of claim 11, wherein each presentation tray further comprises:

a top panel comprising a plurality of apertures, each aperture having a different diameter; and at least one bottom panel slideably mounted to the top panel to move between a 'Closed' position, wherein the at least one bottom panel covers each of the apertures to form the data acquisition cups, and an 'Opened' position, wherein the object sample within the respective data acquisition cup is evacuated and returned to the respective sample container.

14. The system of claim 1, wherein each analysis subsystem further comprises an object return assembly structured and operable to collect each object sample from the respective data acquisition cup and return each object sample to the respective sample container.

15. The system of claim 14, wherein the object return assembly comprises:

a sample transfer funnel structured and operable to collect each object sample from the respective data acquisition cup; and a deceleration and diverter assembly structured and operable to receive each object sample from the sample transfer funnel, via an object transfer tube fluidly connecting the deceleration and diverter assembly with the sample transfer funnel, and divert each sample into one of a plurality of return tubes to return each object sample to the respective object sample container.

16. The system of claim 15, wherein the deceleration and diverter assembly comprises a deceleration chamber having an interior compartment wall including a spiral channel through which each object sample received from the sample transfer funnel will travel to decrease a transfer speed of each respective object sample.

17. The system of claim 16, wherein the deceleration and diverter assembly further comprises a diverter chamber including an interior compartment and diverter gate within the interior compartment, the diverter chamber coupled to the deceleration chamber such that each object sample will pass from the deceleration chamber interior compartment into the diverter chamber interior compartment, the diverter chamber interior compartment having a plurality of exit ports connected to the plurality of return tubes and the diverter gate operable to selectively direct each object sample to a selected one of the return tubes.

18. The system of claim 17, wherein the deceleration and diverter assembly further comprises an accumulator sluice plate slideably mounted between the deceleration chamber and the diverter chamber and controllable between an 'Opened' and 'Closed' position to control the passing of each object sample from the deceleration chamber into the diverter chamber.

19. The system of claim 1, wherein each workstation further comprises a sample container cap handling assembly structured and operable to remove a cap from each sample container prior to the object sample being removed from the respective sample container and replace the cap on each sample container subsequent to returning each object sample to the respective sample container.

20. A method for analyzing a plurality of small objects, said method comprising:
supporting a plurality of sample trays populated with a plurality of arrayed sample containers on a staging console located at a tray staging location adjacent a home end of a guide track for a tray shuttle robot, each sample container containing a respective object sample comprising a plurality of objects;
distributing each sample tray to a corresponding one of a plurality of workstations located adjacent at least one side of the guide track, via automated operation of the tray shuttle robot along the guide track;
sequentially removing each sample container from the respective sample tray and sequentially placing each sample container into a processing assembly of an analysis subsystem of the respective workstation by a 3-axis sample container handling robot of a container transfer subsystem, dispensing each object sample from the respective sample container, obtaining data to determine the volume of the object sample, analyzing each object sample, and depositing each measured object sample into one of a plurality of data acquisition cups of a data collection assembly based on the volume of the respective object sample; and
retrieving the sample trays from each workstation and returning each sample tray to the tray staging location, via automated operation of the tray shuttle robot along the guide track.

21. The method of claim 20, wherein locating a staging console supporting a plurality of sample trays at a tray staging location comprises sequentially locating a plurality of mobile staging consoles at a tray staging location, each mobile staging console supporting a plurality of sample trays.

22. The method of claim 20, wherein distributing each sample tray to a corresponding one of the work station comprises removing each sample tray from the tray staging location and placing each sample tray on a queuing platform of a corresponding one of the workstations, via automated operation of the tray shuttle robot along the guide track.

23. The method of claim 22, wherein placing each sample tray on the queuing platform of the corresponding one of the workstations comprises accurately locating and orienting each sample tray on the queuing platform, such that the location of each respective sample container has particular X-Y coordinates with respect to the queuing platform.

24. The method of claim 23, wherein accurately locating and orienting each sample tray on the queuing platform comprises mating a plurality of tray locating fixture first halves of a docking plate of each respective sample tray queuing platform with a plurality of tray locating fixture second halves of a bottom plate of each sample tray.

25. The method of claim 23, wherein accurately locating and orienting each sample tray on the queuing platform comprises controllably engaging a tray locking mechanism first half of each sample tray queuing platform with, a tray locking mechanism second half of a bottom plate of each respective sample tray to steadily retain each sample tray on the docking plate of the respective sample tray queuing platform when distributed by the tray shuttle robot.

26. The method of claim 20, wherein sequentially removing each sample container from the respective sample tray further comprises reading a sample identification device associated with each sample container as the sample container handling robot moves each sample container from the respective sample tray to the processing assembly of the respective workstation.

27. The method of claim 20, wherein sequentially removing each object sample from the respective sample container comprises rotating a container retention block of the respective processing assembly to dispense each respective sample into a dispensing funnel of the respective processing assembly.

28. The method of claim 27, wherein sequentially removing each object sample from the respective sample container further comprises removing a cap from each respective sample container prior to dispensing each sample in the respective dispensing funnel utilizing an automated sample container cap handling assembly of the respective workstation.

29. The method of claim 27, wherein analyzing each object sample comprises:
depositing each sample into a measuring chamber of a height measurement module of the respective processing assembly, via the respective dispensing funnel, each respective measuring chamber having a predetermined cross-sectional area;
measuring the height of each sample within the measuring chamber; and
determining the volume of each respective sample volume using the cross-sectional area of the measuring chamber and the measured height of each respective object sample within the measuring chamber.

30. The method of claim 29, wherein analyzing each object sample further comprises:
depositing each object sample into one of a plurality of different size data acquisition cups within a presentation tray of the respective workstation analysis subsystem based on the volume of the respective object sample; and
acquiring data of each object sample within the respective data acquisition cup.

31. The method of claim 30, wherein depositing each object sample into one of the different size data acquisition cups comprises moving a retractable bottom of the respective measuring chamber from a 'Closed' position in which each respective object sample is retained within the measuring chamber to an 'Opened' position in which each object sample is dispensed from the respective measuring chamber into the respective data acquisition cup.

32. The method of claim 30, wherein acquiring data of each object sample within the respective data acquisition cup comprises moving each data acquisition cup and respective object sample deposited therein within a measurement field of a data collection instrument of the respective workstation, via an automated X-Y stage having the presentation tray mounted thereto.

33. The method of claim 30, wherein returning each object sample to the respective sample container comprises:
 depositing each object sample from the respective data acquisition cup into a sample transfer funnel of an object return assembly of the respective workstation;
 transferring each object sample from the sample transfer funnel to a deceleration and diverter assembly of the respective object return assembly; and
 diverting each sample into one of a plurality of return tubes of the object return assembly to return each object sample to the respective object sample container.

34. The method of claim 33, wherein depositing each object sample from the respective data acquisition cup into the sample transfer funnel comprises moving at least one bottom panel slideably mounted to a top panel of the respective presentation tray from a 'Closed' position, wherein the at least one bottom panel provides a bottom for each of the data acquisition cups in the respective presentation tray, to an 'Opened' position, wherein the object sample within the respective data acquisition cup is evacuated into the respective sample transfer funnel.

35. The method of claim 33, wherein transferring each object sample from the sample transfer funnel to a deceleration and diverter assembly comprises:
 directing each object sample received from the sample transfer funnel into a deceleration chamber of the respective deceleration and diverter assembly; and
 traversing each object sample along a spiral channel formed in a wall of an interior compartment of the deceleration chamber to decrease a transfer speed of each respective object sample.

36. The method of claim 35, wherein diverting each sample into one of a plurality of return tubes of the object return assembly to return each object sample to the respective object sample container comprises selectively positioning a diverter gate, movably mounted within an interior compartment of a diverter chamber connected to the deceleration chamber, to direct each object sample to one of a plurality of exit ports of the diverter chamber, each exit port connected a respective one of the return tubes.

37. The method of claim 36, wherein returning each object sample to the respective sample container further comprises controlling the passing of each object sample from the deceleration chamber into the diverter chamber using an accumulator sluice plate slideably mounted between the deceleration chamber and the diverter chamber and controllable between an 'Opened', in which the respective object sample is allowed to pass from the deceleration chamber into the diverter chamber, and 'Closed' position, in which the respective object sample is prevented from passing from the deceleration chamber into the diverter chamber.

38. The method of claim 20 wherein sequentially returning each sample container to the respective sample tray comprises replacing a cap on each respective sample container subsequent to returning each object sample to the respective sample container utilizing an automated sample container cap handling assembly of the respective workstation.

39. A system for analyzing a plurality of small objects, said system comprising:
 a plurality of workstations structured and operable to analyze each of a plurality of object samples, each object sample comprising a plurality of objects, each workstation including:
  a robotic container transfer subsystem and an automated analysis subsystem, wherein the robotic container transfer subsystem is structured and operable to:
   sequentially transfer each of a plurality of sample containers from at least one of a plurality of sample trays to the automated analysis subsystem, and
   subsequently transfer each of the sample containers from the automated analysis subsystem back to the respective sample tray, and
  wherein the automated analysis subsystem structured and operable to:
   sequentially receive each sample container from the container transfer subsystem;
   determine a volume of the object sample within each respective sample container;
   deposit each object sample within a selected one of a plurality of different size sample cups based on the volume of the respective sample;
   acquire data of each respective object sample; and
   return each object sample to the respective sample container; and
 a tray shuttle robot structured and operable to distribute and retrieve the sample trays to and from each of the plurality of workstations.

40. A system for analyzing a plurality of seeds, said system comprising:
 a plurality of workstations structured and operable to analyze a plurality of selected seed samples, each workstation including:
  a robotic container transfer subsystem comprising:
   a 3-axis sample container handling robot structured and operable to sequentially remove and replace each of a plurality of sample containers arrayed in at least one sample container tray, each sample container retaining a respective seed sample comprising a plurality of seeds; and
   a bar code scanning module structured and operable to read a bar code affixed to each sample container removed from the respective sample container tray by the sample container handling robot 38, each bar code providing a unique ID relating to each respective sample container; and
  an automated analysis subsystem comprising:
   at least two parallel sample processing assemblies structured and operable to determine the volume of each seed sample within each respective sample container removed from the respective tray and placed in the respective sample processing assembly by the sample container handling robot, and deposit the seed into a particular one of a plurality of different size sample cups based on the volume of the respective seed sample; and
   an near infra-red (NIR) analysis module structured and operable to NIR scan each seed sample deposited into the sample cups and communicate data acquired by each NIR scan to a master control system where the data is associated with the unique ID of the respective sample container 14 and stored in a database; and a tray shuttle robot structured and operable to distribute and retrieve the sample trays to and from each of the plurality of workstations.

\* \* \* \* \*